United States Patent [19]

Misra et al.

[11] Patent Number: 4,555,520

[45] Date of Patent: Nov. 26, 1985

[54] 2-PYRIDYLCARBOXAMIDES WHICH INHIBIT ARACHIDONIC ACID RELEASE

[75] Inventors: Raj N. Misra, Princeton; Donald S. Karanewsky, East Windsor, both of N.J.

[73] Assignee: E. R. Squibb & Sons, Inc., Princeton, N.J.

[21] Appl. No.: 642,006

[22] Filed: Aug. 20, 1984

[51] Int. Cl.⁴ .................. C07D 213/81; A61K 31/455
[52] U.S. Cl. ................................ 514/346; 514/354; 546/291; 546/323
[58] Field of Search .............. 546/291, 323; 424/266; 514/346, 354

[56] References Cited

PUBLICATIONS

Bach; M. K., "Prospects for the Inhibition of Leukotriene Synthesis," *Biochemical Pharmacology*, vol. 33, No. 4, pp. 512–521, (1984).
Samuelsson; B., "Leukotrienes: Mediators of Immediate Hypersensitivity Reaction and Inflammation", *Science*, vol. 220, pp. 568–575, (1983).
Samuelsson; B., "The Leukotrienes, Highly Biologically Active Substances Involved in Allergy and Inflammation", *Angew Chem. Int. Ed. Engl.*, 21 (1982), pp. 902–910.
Ford-Hutchinson; A. W., "Leukotriene Involvement in Pathologic Processes", *J. Allergy Clin. Immunol.*, Sep. 1984.
Kuehl; F. A., et al., "Interactions Between Prostaglandins and Leukotrienes", *Biochemical Pharmacology*, vol. 33, No. 1, pp. 1–5, (1984).

*Primary Examiner*—Henry R. Jiles
*Assistant Examiner*—Dale A. Bjorkman
*Attorney, Agent, or Firm*—Lawrence S. Levinson; Burton Rodney

[57] ABSTRACT

2-Pyridylcarboxamides are provided having the structure

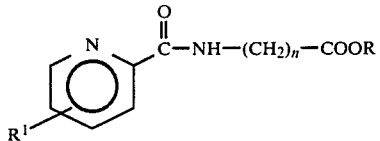

wherein n is 1 to 10;
R is hydrogen, lower alkyl, alkali metal or an amine salt; and
$R^1$ is $C_6$–$C_{20}$ alkyl, $C_6$–$C_{20}$ alkenyl, $C_6$ to $C_{20}$ alkoxy or phenyl. These compounds are useful as inhibitors of arachidonic acid release and as such are useful as antiallergy agents.

21 Claims, No Drawings

2-PYRIDYLCARBOXAMIDES WHICH INHIBIT ARACHIDONIC ACID RELEASE

DESCRIPTION OF THE INVENTION

The present invention relates to 2-pyridylcarboxamides which are inhibitors of arachidonic acid release and prevent prostaglandin and leukotriene $C_4$ formation in macrophages and as such are useful, for example, as antiallergy agents. These compounds have the structural formula

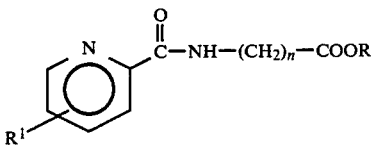

wherein n is 1 to 10, R is hydrogen or lower alkyl, and $R^1$ is $C_6$-$C_{20}$ alkyl, $C_6$-$C_{20}$ alkenyl, $C_6$-$C_{20}$ alkoxy or phenyl. The $R^1$ group may be in the 3, 4, 5 or 6 position on the pyridine ring, with the 4 or 5 position being preferred.

The compounds of formula I will form salts with an alkali metal, such as lithium, sodium or potassium as well as with dicyclohexylamine or other amines, tris(-hydroxymethyl)aminomethane and other amines as set out in U.S. Pat. No. 4,294,759.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "$C_6$-$C_{20}$ alkyl" as employed herein includes the above alkyl radicals of 6 carbons and more as well as alkyl radicals of up to 20 carbon atoms, preferably from 8 to 14 carbons, such as in addition to the $C_6$ to $C_{12}$ alkyl radicals set out above, tridecyl, tetradecyl, pentadecyl, hexadecyl, heptadecyl, octadecyl, nonadecyl, eicosanyl including all isomers thereof with or without the above substituents.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), and/or 1 or 2 lower alkoxy groups.

The term "aralkyl", "aryl-alkyl" or "aryl-lower alkyl" as used herein refers to lower alkyl groups as discussed above having an aryl substituent, such as benzyl.

The term "$C_6$-$C_{20}$ alkenyl" or "alkenyl" includes straight or branched chain radicals of from 6 to 20 carbons, preferably 8 to 14 carbons in the normal chain, which include one double bond in the normal chain, such as 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 2-tridecenyl, 3-tetradecenyl, 1-pentadecenyl, 2-hexadecenyl, 4-heptadecenyl, 7-octadecenyl, 6-nonadecenyl and 8-eicosenyl, including all isomers thereof and the like.

The term "lower alkoxy", "alkoxy" or "aralkoxy" includes any of the above lower alkyl, alkyl or aralkyl groups linked to an oxygen atom.

The term "$C_6$ to $C_{20}$ alkoxy" refers to any of the $C_6$ to $C_{20}$ alkyl groups, preferably $C_8$ to $C_{14}$ alkoxy groups, linked to an oxygen atom.

The term "halogen" or "halo" as used herein refers to chlorine, bromine, fluorine or iodine with chlorine being preferred.

Preferred are those compounds of the invention wherein $R^1$ is in the 4- or 5-position and is n-decyl, n-tridecyl, 1-decenyl or phenyl, n is 1 to 4, and R is hydrogen or ethyl.

The various compounds of the invention of formula I may be prepared as described below.

The substituted pyridine of the structure A

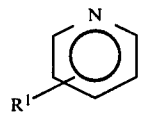

is subjected to an oxidation reaction by reacting A with an oxidizing agent such as meta-chloroperbenzoic acid, in the presence of an inert organic solvent such as methylene chloride, at reduced temperatures of from about $-10°$ to about $0°$ C., to form the N-oxide of formula II

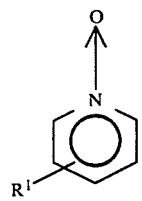

A solution of the N-oxide II, base such as triethylamine, and trimethylsilylcyanide in acetonitrile, is heated at reflux (bath temperature 100° C.) for a period of from about 12 to about 48 hours to form the nitrile of formula III

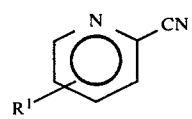

Nitrile III is next hydrolyzed by treating III with an alkali metal hydroxide such as sodium hydroxide, potassium hydroxide or lithium hydroxide in the presence of an aqueous-alcoholic solvent to form the corresponding 2-pyridinecarboxylic acid IV

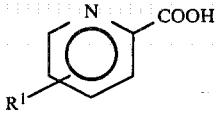

IV

Acid IV is then subjected to an aminoester coupling reaction wherein a solution of acid IV in an inert organic solvent, such as tetrahydrofuran or methylene chloride is treated with an activating agent, such as diethyl chlorophosphate or ethyl chloroformate, followed by base, such as triethylamine, a salt of an ester of an amino acid having the structure V $$H_2N-(CH_2)_n-CO_2R^2 \cdot HX \quad V$$

wherein X is Cl, Br or F and $R^2$ is lower alkyl, and more base such as triethylamine. The reaction is stirred at room temperature for a period of from about 3 to about 5 hours to form an ester of the invention having the structure IA

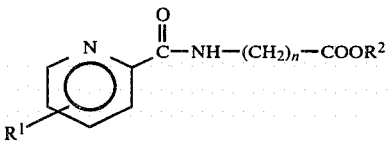

IA (wherein $R^2$ is lower alkyl).

The ester IA may be converted to the corresponding acid of the invention IB

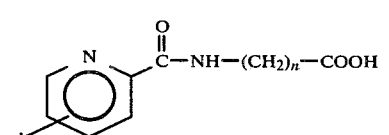

IB by treating the ester IA with an alkali metal hydroxide such as lithium or sodium hydroxide to form the corresponding alkali metal salt followed by neutralization with an acid, such as dilute hydrochloric acid or oxalic acid to form the acid IB.

The tris(hydroxymethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

Where $R^1$ in compounds I, IA or IB of the invention is phenyl, then the starting material A will have the structure $A^I$

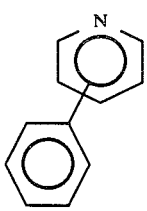

$A^I$ which represents known commercially available compounds.

Where $R^1$ in compounds I, IA or IB of the invention is $C_6$ to $C_{20}$ alkenyl, then the starting pyridine compound $A^{II}$

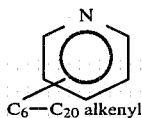

$A^{II}$ may be prepared by subjecting a pyridinecarboxaldehyde of the structure B

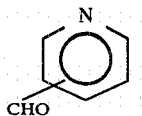

B to a Wittig reaction wherein B is treated with a phosphorane generated by addition of n-butyllithium to a phosphonium salt of structure C $$R'_a-P^{\oplus}-(C_6H_5)_3Br^{\ominus} \quad C$$
(wherein $R'_a$ is an alkyl group containing one less carbon then $R^1$)

dissolved in an inert organic solvent such as tetrahydrofuran, to form compound $A^{III}$

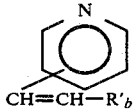

$A^{III}$ wherein $R'_b$ is an alkyl group which contains two less carbons than the $R^1$ alkenyl group so that —CH=CH—$R'_b$ is equivalent to $R^1$ which is $C_6$–$C_{20}$ alkenyl.

Where $R^1$ in compounds of formula I, IA or IB is $C_6$ to $C_{20}$ alkyl, then the starting pyridine compound $A^{IV}$ may be prepared by hydrogenating compound $A^{III}$ by treating with hydrogen in the presence of palladium on charcoal to form the pyridine derivative $A^{IV}$

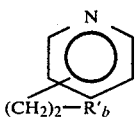

$A^{IV}$ wherein $(CH_2)_2$—$R'_b$ is equivalent to $R^1$ which is $C_6$ to $C_{20}$ alkyl.

Where $R^1$ in compounds of formula I, IA or IB is $C_6$ to $C_{20}$ alkoxy, then the starting material $A^V$

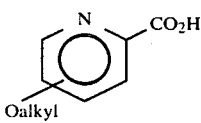

$A^V$ may be prepared by reacting the chloropyridine N-oxide D

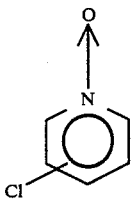

with an appropriate alkanol (alkyl—OH) in the presence of a base such as sodium hydride, or potassium hydride and an inert organic solvent such as dimethylformamide, to form N-oxide VI

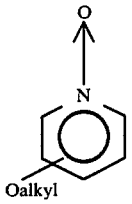   VI which is reacted with trimethylsilylcyanide E (CH₃)₃SiCN   E in the presence of triethylamine and acetonitrile to form the nitrile VII

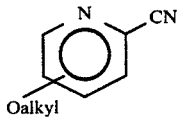   VII

Nitrile VII is next treated with strong base such as alkali metal hydroxide like NaOH, KOH or LiOH in the presence of aqueous ethanol to form the acid $A^{IV}$.

The compounds of the invention are inhibitors of arachidonic acid release and prevent prostaglandin and leukotriene C₄ formation in macrophages (Samuelsson, B., Science, Vol. 220, p. 568–575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma.

An effective but essentially non-toxic quantity of the compound is employed in treatment.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in °C. TLC plates were visualized by spraying and heating with 5% phosphomolybdic acid in ethanol.

EXAMPLE 1

[[(4-Decyl-2-pyridinyl)carbonyl]amino]acetic acid, ethyl ester

A. 4-(1-Decenyl)pyridine

A solution of 20.2 g (36.8 mmol, 1.3 eq) of 1-triphenylphosphononyl bromide dissolved in 100 ml THF was cooled to −78° C. and 11.9 ml (31.1 mmol, 1.1 eq, 2.6M in hexane) of n-BuLi was added dropwise. This was followed by the dropwise addition of 2.70 ml (156 mmol, 5.5 eq) of hexamethylphosphoroustriamide (HMPA). The solution was stirred for 10 minutes. A solution of 3.0 g (28 mmol) of 4-pyridine carboxaldehyde in 41 ml THF was added. The resulting solution was warmed to room temperature and stirred for 1.75 hours. Water was added to the reaction and this was extracted with Et₂O. The organic layer was washed with saturated NH₄Cl, followed by saturated NaCl and dried (Na₂SO₄). The solution was filtered and concentrated in vacuo. Hexanes were added to the residue, decanted and concentrated. The crude material was purified by flash chromatography (15×3 cm, silica gel, 1:5 EtOAc/hexanes) to yield 4.78 g (78%) of title compound as a yellow oil.

IR (0.2 mm cells, CCl₄): 3071, 3018, 2958, 2927, 2855, 1595, 1545, 1465, 1378, 992 cm⁻¹.

¹H NMR (CDCl₃) δ 0.86–2.30 (br m, 17H); 5.80 (dt, J=12.6 Hz, 1H); 6.30 (d, J=12 Hz, 1H); 7.10 (m, 2H); 8.59 (m, 2H).

TLC (1:2 EtOAc/hexanes) $R_f$=0.72, UV.

B. 4-n-Decenylpyridine

To a suspension of 0.92 g 10% Pd/C and 20 ml MeOH was added 4.60 g (21.4 mmol) of title A compound in 100 ml MeOH. The suspension was shaken under hydrogen (Parr) for 4 hours. The reaction mixture was filtered through Celite and washed several times with MeOH. The volatiles were evaporated in vacuo to yield 4.50 g (92%) of title compound as a dark orange oil.

IR (0.2 mm cells, CCl₄): 3069, 3028, 2927, 2855, 1601, 1555, 1464, 1377 cm⁻¹.

270 MHz ¹H NMR (CDCl₃) δ 0.87 (t, 3H), δ 1.25 (m, 14H), δ 1.67 (br m, 2H), δ 2.59 (t, 2H), δ 7.09 (d, J=5 Hz, 2H), δ 8.47 (d, J=5 Hz, 2H).

Partial 270 MHz ¹³C NMR (CDCl₃) δ 123.87 (para-C), 149.62 (meta-C), 151.51 (ortho-C).

TLC (1:9 MeOH/CH₂Cl₂) $R_f$ 0.44, UV

C. 4-n-Decylpyridine-N-oxide

A solution containing 4.16 g (19.5 mmol) of title B compound in 100 ml of CHCl₃ was cooled to 0° C. and 3.90 g (19.5 mmol) of meta-chloroperbenzoic acid in 50 ml of CHCl₃ was added. The temperature was maintained at 0° C. for 1 hour 45 minutes. Then 0.39 g of additional meta-chloroperbenzoic acid was added and solution was warmed to room temperature and stirred under argon overnight. The reaction mixture was filtered through a column of basic alumina (20 times the amount of the combined starting materials), eluted first with CHCl$_3$ followed by 1:3 MeOH/CHCl$_3$. The MeOH/CHCl$_3$ eluant was concentrated in vacuo and purified by flash chromatography (25×9 cm, silica gel, 1:2 EtOAc/hexanes, then MeOH) to give 3.54 g (74%) of a dark brown oil which solidified: m.p. 36°–38° C.

IR (film) 3060, 3000, 2900, 2840, 1475, 1440, 1260, 1210 cm$^{-1}$.

$^1$H NMR (CDCl$_3$) δ 0.93–1.60 (br m, 19H); 2.60 (m, 2H); 7.10 (m, 2H); 8.15 (m, 2H).

TLC (1:9 MeOH/CH$_2$Cl$_2$) R$_f$=0.67, UV, PMA.

D. 2-Cyano-4-n-decylpyridine

To a solution of 3.54 g (14.2 mmol) of title C compound in 80 ml of dry CH$_3$CN was added 3.0 ml (21.3 mmol, 1.5 eq) of triethylamine. The solution was stirred at room temperature and 5.7 ml (42.6 mmol, 3 eq) of trimethylsilyl cyanide was added dropwise. The reaction was heated to 100° C. and stirred for 26 hours. Then an additional 3.0 ml (21.3 mmol, 1.5 eq) of triethylamine was added, followed by 3.8 ml (28.4 mmol, 2 eq) of trimethylsilyl cyanide and heating was continued for 16 hours. Reaction was cooled to room temperature and 30 ml of H$_2$O was added slowly. The solution was extracted with EtOAc, which was washed with 1N NaOH, dried (Na$_2$SO$_4$), filtered and concentrated in vacuo. The crude material was purified via flash chromatography (25×9 cm, silica gel, 2 L, 1:1 EtOAc/hexanes, 1 L MeOH) to yield 2.64 g (70%) of title compound as a yellow oil.

IR (film) 3030, 2990, 2280, 1640, 1480, 1400 cm$^{-1}$.

$^1$H NMR (CDCl$_3$) δ 0.40–2.00 (m, 19H); 2.70 (m, 2H); 7.36 (m, 1H); 7.53 (s, 1H); 8.58 (d, J=5 Hz, 1H).

TLC (1:9 MeOH/CH$_2$Cl$_2$) R$_f$=0.69, UV.

E. 4-Decyl-2-pyridinecarboxylic acid

To a solution containing 2.25 g (9.22 mmol) of title D compound in 50 ml EtOH, was added an equal volume of 10N NaOH. The reaction was refluxed to 3.75 hours, then cooled to room temperature and acidified with glacial acetic acid to a pH of approximately 5. The solution was poured into H$_2$O and extracted with EtOAc, dried (Na$_2$SO$_4$), filtered and concentrated in vacuo. The resulting solid was filtered and washed with Et$_2$O to yield 2.09 g (86%) of title acid as an off-white solid: m.p. 89°–90° C.

IR (KBr Pellet) 3429, 2960, 2846, 1697, 1603, 1459, 1415, 1378 cm$^{-1}$.

270 MHz $^1$H NMR (CDCl$_3$) δ 0.87 (crude t, 3H); 1.25 (m, 14H); 1.67 (m, 2H); 2.73 (t, J=8 Hz, 2H); 7.39 (d, J=4 Hz, 1H); 8.08 (s, 1H); 8.53 (d, J=4 Hz, 1H); 8.87 (br s, 1H).

TLC (1:1:8 MeOH/HOAc/CH$_2$Cl$_2$) R$_f$=0.52 (tails), UV.

Microanalysis calc'd for C$_{16}$H$_{25}$NO$_2$: C, 72.97; H, 9.57; N, 5.32. Found: C, 72.98; H, 9.68; N, 5.14.

F. [[(4-Decyl-2-pyridinyl)carbonyl]amino]acetic acid, ethyl ester

A solution of 0.20 g (0.76 mmol) of title E acid in 10 ml of dry THF was cooled to 0° C. and 0.11 ml (0.76 mmol, 1 eq.) of diethylchlorophosphate was added, followed by 0.10 ml (0.76 mmol, 1 eq) of triethylamine. The reaction was warmed to room temperature and stirred for 1 hours. To this solution was added 0.11 g (0.84 mmol, 1.1 eq.) of glycine ethyl ester hydrochloride (Aldrich, G650-3) followed by 0.11 ml (0.84 mmol, 1.1 eq) of triethylamine. The reaction was stirred at room temperature for 18 hours then filtered through a column of basic alumina (activity 1) eluting with EtOAc. The filtrate was concentrated in vacuo and the crude material purified by flash chromatography (9×3 cm, silica gel, 1:30 MeOH/CH$_2$Cl$_2$) to yield 0.23 g (92%) of title product as a white solid; m.p. 29°–30° C.

IR (KBr pellet) 3363, 2924, 2851, 1748, 1667, 1604, 1529, 1467, 1412, 1376, 1198 cm$^{-1}$.

270 MHz $^1$H NMR (CDCl$_3$) δ 0.89 (crude t, 3H, —(CH$_2$)$_9$—CH$_3$); δ 1.29 (m, 17H, —CO$_2$CH$_2$—CH$_3$, —(CH$_2$)$_7$—CH$_3$); 1.66 (m, 2H, —CH$_2$—CH$_2$—nC$_8$H$_{17}$); 2.67 (t, J=7 Hz, 2H, —CH$_2$—nC$_9$H$_{19}$); 4.24 (overlapping q and t, 2H, —NH—CH$_2$—CO$_2$CH$_2$CH$_3$); 7.25 (d, J=6 Hz, 1H, ring H$_5$); 8.01 (s, 1H, ring H$_3$); 8.42 (d, J=6 Hz, 1H, ring H$_6$); 8.44 (s, 1H, —NH—);

TLC: R$_f$ (silica gel, 1:1 EtOAc/petroleum ether)=0.70, U.V.

Microanalysis calcd for C$_{20}$H$_{32}$N$_2$O$_3$: C, 68.94; H, 9.26; N, 8.04. Found: C, 68.79; H, 9.35; N, 8.08.

EXAMPLE 2

2-[[(4-Decyl-2-pyridinyl)carbonyl]amino]acetic acid

A solution of 0.10 g (0.28 mmol) of ester prepared as described in Example 1 and 0.02 g (0.5 mmol) LiOH·H$_2$O in 4 ml of THF and 1 ml of H$_2$O was stirred at room temperature for 2.5 hours. To this solution was added 1.5 eq. of glacial acetic acid; the reaction mixture was poured in H$_2$O and extracted with Et$_2$O. The organic layers were combined, dried (Na$_2$SO$_4$) and concentrated in vacuo to yield 0.66 g (72%) title product as a white solid: m.p. 79°–81° C.

IR (KBr pellet) 3392 (broad), 2915, 2851, 1709, 1671, 1605, 1511, 1465, 1424, 1409, 1242 cm$^{-1}$.

270 MHz $^1$H NMR (CDCl$_3$)δ 0.87 (crude t, 3H, —(CH$_2$)$_9$—CH$_3$); δ 1.25 (m, 14H, —CH$_2$—(CH$_2$)$_7$—CH$_3$); 1.64 (crude t, 2H, —CH$_2$CH$_2$—nC$_8$H$_{17}$); 2.67 (t, J=7 Hz, —CH$_2$—nC$_9$H$_{19}$); 4.32 (d, J=5 Hz, 2H, —NH—CH$_2$CO$_2$H); 7.25 (crude d, J=3 Hz, 1H, ring H$_5$); 8.03 (s, 1H, ring H$_3$); 8.44 (d, J=5 Hz, 1H, ring H$_6$); 8.57 (crude t, 1H, —NH—); 10.45 (br s, 1H, —CO$_2$H).

TLC: R$_f$(silica gel, 1:9 MeOH/CH$_2$Cl$_2$)=0.13 (tails), U.V.

Microanalysis calcd for C$_{18}$H$_{28}$N$_2$O$_3$: C, 67.47; H, 8.81; N, 8.74. Found: C, 67.50; H, 8.96; N, 8.49.

EXAMPLE 3

3-[[(4-Decyl-2-pyridinyl)carbonyl]amino]propanoic acid, ethyl ester

A solution of 0.80 g (3.0 mmol) of 4-decyl-2-pyridinecarboxylic acid prepared as described in Example 1 Parts A–E and 15 ml of dry THF was cooled to 0° C and 0.29 ml (3.0 mmol, 1 eq) of diethyl chlorophosphate was added, followed by 0.42 ml (3.0 mmol, 1 eq.) of triethylamine. The reaction was warmed to room temperature and stirred for 1 hour. To this solution was added 0.51 g (3.3 mmol, 1.1 eq) of β-alanine ethyl ester hydrochloride (prepared by bubbling hydrogen chloride through an ethanol solution of β-alanine then diluting with ether and collecting the precipitated product) followed by 0.47 ml (3.3 mmol, 1.1 eq) of triethylamine. The reaction was stirred for 6 hours at room temperature then filtered through a column of basic alumina (activity 1) eluting with CHCl$_3$ then MeOH. The filtrates were combined and concentrated in vacuo. Petroleum ether was added to the residue and a white precipitate formed. This was filtered and the filtrate was concentrated in vacuo to yield a yellow oil. Purification was achieved via flash chromatography (9×3 cm, silica gel, 1:7 EtOAc/petroleum ether) to yield 0.54 g (49%) of title ester as a light yellow oil.

IR (CCl4, 0.2 mm cells) 3402, 2927, 2855, 1733, 1677, 1604, 1517, 1464, 1372, 1185 cm$^{-1}$.

270 MHz $^1$H NMR (CDCl$_3$) δ 0.88 (m, 3H, —(CH$_2$)$_9$—CH$_3$); δ 1.34 (m, 17H, —(CH$_2$)$_7$—CH$_3$, and —CO$_2$CH$_2$CH$_3$); 1.64 (m, 2H, —CH$_2$—CH$_2$—(CH$_2$)$_7$—CH$_3$); 2.78 (m, 4H, —CH$_2$—CO$_2$CH$_2$CH$_3$, —CH$_2$(CH$_2$)$_8$CH$_3$); 3.75 (dt, J=6 Hz, 2H, —N-H—CH$_2$); 4.18 (q, J=6 Hz, 2H, —CO$_2$CH$_2$CH$_3$); 7.12 (crude d, J=6 Hz, 1H, ring H$_5$); 7.93 (s, 1H, ring H$_3$); 8.33 (d, J=6 Hz, ring H$_6$ with broad s—NH underneath, 2H).

TLC: R$_f$ (silica gel, 1:1 EtOAc/petroleum ether)=0.53, UV, PMA.

Microanalysis Calcd for C$_{21}$H$_{34}$N$_2$O$_3$: C, 69.58; H, 9.45; N, 7.73. Found: C, 69.85; H, 9.55; N, 7.69.

EXAMPLE 4

3-[[(4-Decyl-2-pyridinyl)carbonyl]amino]propanoic acid

A solution of 0.20 g (0.55 mmol) of ester prepared as described in Example 3, 0.05 g (1 mmol, 2 eq.) of LiOH·H$_2$O in 4 ml of THF, and 1 ml of H$_2$O was stirred at room temperature for 4.5 hours. A slight excess (1.5 eq) of glacial acetic acid was added. The reaction was poured into H$_2$O and extracted with Et$_2$O. The organic layers were combined, dried (Na$_2$SO$_4$), and concentrated in vacuo. Hexanes were added to the residue and the flask was cooled. The resulting white solid was collected to yield 171 mg (93%) of title acid: m.p. 64°-67° C.

IR (KBr pellet) 3399 (broad), 3310, 2916, 2849, 1723, 1641, 1603, 1544, 1467, 1177 cm$^{-1}$.

270 MHz $^1$H NMR (CDCl$_3$) δ 0.87 (crude t, 3H, —(CH$_2$)$_7$—CH$_3$); δ 1.27 (m, 14H, —(CH$_2$)$_7$—CH$_3$); 1.75 (crude t, 2H, —CH$_2$—nC$_8$H$_{17}$); 2.67 (t, 2H, J=6 Hz, —NHCH$_2$CH$_2$CO$_2$H); 2.75 (t, 2H, J=6 Hz, —CH$_2$—nC$_9$H$_{19}$); 3.76 (dt, 2H, J=6 Hz, —NH—CH$_2$—); 7.23 (m, 1H, ring H$_5$); 8.02 (s, 1H, ring H$_3$); 8.39 (d, J=6 Hz, 1H, ring H$_6$); 8.41 (crude t, 1H, —NH—); ~9.70 (br s, 1H, —CO$_2$H).

TLC: R$_f$(silica gel, 1:9 MeOH/CH$_2$Cl$_2$)=0.31, U.V.

Microanalysis Calcd for C$_{19}$H$_{30}$N$_2$O$_3$: C, 68.24; H, 9.04; N, 8.38. Found: C, 68.27; H, 9.09; N, 8.29.

EXAMPLE 5

4-[[(4-Decyl-2-pyridinyl)carbonyl]amino]butanoic acid, ethyl ester

A solution of 500 mg (1.90 mmol) of 4decyl-2-pyridinecarboxylic acid prepared as described in Example 1 Parts A to E and 20 ml of THF was cooled to 0° C. and 180 μl (1.90 mmol, 1 eq) of diethyl chlorophosphate was added, followed by 270 μl (1.90 mmol, 1 eq) of triethylamine. The reaction was warmed to room temperature and stirred for 1 hour. To this soluiton was added 350 mg (2.09 mmol, 1.1 eq) of ethyl 4-aminobutyrate hydrochloride, followed by 290 μl (2.09 mmol, 1.1 eq) of triethylamine. The reaction was stirred for 5 hours at room temperature and then filtered through a column of basic alumina (activity I). The column was washed with EtOAc, CHCl$_3$ and MeOH. The eluants were combined, concentrated in vacuo then purified via flash chromatography (9×3 cm, silica gel, 1:20 MeOH/CH$_2$Cl$_2$) to yield 330 mg (46%) of title ester as a yellow oil.

IR (0.2 mm cells, CCl$_4$) 3398, 2929, 2855, 1735, 1678, 1604, 1521, 1464, 1374, 1288, 1250, 1176 cm$^{-1}$.

270 MHz $^1$H NMR (CDCl$_3$) δ 0.87 (t, 3H); 1.22 (m, 17H); 1.62 (m, 2H); 1.97 (tt, J=7, 7 Hz, 2H); 2.41 (t, J=7 Hz, 2H); 2.66 (t, J=7 Hz, 2H); 3.52 (dt, J=7, 7 Hz, 2H); 4.12 (q, J=7 Hz, 2H); 7.21 (dd, J=2, 5 Hz, 1H); 8.01 (s, 1H); 8.12 (br s, 1H); 8.39 (d, J=5 Hz, 1H);

TLC (silica gel, 1:9 MeOH/CH$_2$Cl$_2$) R$_f$=0.88.

Microanalysis Calcd for C$_{22}$H$_{36}$N$_2$O$_3$: C, 70.17; H, 9.63; N, 7.44. Found: C, 70.27; H, 9.91; N, 7.07.

EXAMPLE 6

4-[[(4-Decyl-2-pyridinyl)carbonyl]amino]butanoic acid

A solution of 0.20 g (0.53 mmol) of ester prepared as described in Example 5 in 4 ml of THF, 1 ml of H$_2$O and 0.05 g (1 mmol, 2 eq) of LiOH.H$_2$O was stirred at room temperature under argon for 5 hours, then 1.5 eq of glacial acetic acid was added to the solution (pH~4-5). The resulting solution was poured into H$_2$O and extracted with Et$_2$O. The organic layers were combined, dried (Na$_2$SO$_4$) and concentrated in vacuo. Petroleum ether was added to the residue and a white solid precipitated to yield 0.15 g (81%) of title acid: m.p. 72°-74° C.

IR (KBr Pellet) 3395, 3307, 2919, 2850, 1706, 1652, 1608, 1540, 1467, 1450, 1416, 1264 cm$^{-1}$.

270 MHz $^1$H NMR(CDCl$_3$) δ 0.87 (t, 3H, —(CH$_2$)$_9$CH$_3$); δ 1.16 (m, 14H, —(CH$_2$)$_7$—CH$_3$); 1.64 (m, 2H, —CH$_2$(CH$_2$)$_7$—CH$_3$); 1.99 (tt, J=7 Hz, 2H, —NHCH$_2$—CH$_2$—CH$_2$); 2.47 (t, J=7 Hz, 2H, —CH$_2$CO$_2$H); 2.67 (t, J=7 Hz, 2H, —CH$_2$(CH$_2$)$_8$)—CH$_3$); 3.53 (dt, 2H, —NH—CH$_2$—CH$_2$—); 7.23 (d, J=4 Hz, 1H, ring H$_5$); 8.03 (s, 1H, ring H$_3$); 8.27 (crude t, 1H, —NH—); 8.39 (d, J=4 Hz, 1H, ring H$_6$).

TLC: R$_f$(silica gel, 1:9 MeOH/CH$_2$Cl$_2$) 0.40, UV.

Microanalysis Calcd for C$_{20}$H$_{32}$N$_2$O$_3$: C, 68.94; H, 9.26; N, 8.04. Found: C, 68.97; H, 9.37; N, 7.99.

EXAMPLE 7

5-[[(4-Decyl-2-pyridinyl)carbonyl]amino]pentanoic acid, ethyl ester

A solution of 0.50 g (1.9 mmol) of 4-decyl-2-pyridinecarboxylic acid prepared as described in Example 1 Parts A to E and 20 ml of THF was cooled to 0° C. and 0.18 ml (1.9 mmol, 1 eq) of diethyl chlorophosphate was added, followed by 0.27 ml (1.9 mmol, 1 eq) of triethylamine. The reaction was warmed to room temperature and stirred for 1 hour. To this solution was added 0.38 g (2.09 mmol, 1.1 eq) of ethyl 5-aminovalerate hydrochloride (prepared by bubbling hydrogen chloride into an ethanol solution of 5-aminovaleric acid then diluting with ether and collecting the precipitated solid) followed by 0.29 ml (2.1 mmol, 1.1 eq) of triethylamine. The reaction was stirred for 6 hours at room temperature and filtered through a column of basic alumina (activity I), eluting with EtOAc. Purification was accomplished via flash chromatography (silica gel, 1:7 EtOAc/hexanes) to yield 0.39 g (53%) of title ester as a yellow oil.

IR (0.2 mm cells, CCl$_4$) 3401, 2928, 2856, 1736, 1679, 1605, 1524, 1464 cm$^{-1}$.

270 MHz $^1$H NMR (CDCl$_3$) δ 0.88 (m, 3H, —(CH$_2$)$_9$—CH$_3$); δ 1.25 (m, 15H, —CO$_2$—CH$_2$—CH$_3$, —(CH$_2$)$_6$—CH$_2$); 1.69 (br m, 6H, —NHCH$_2$—(CH$_2$)$_2$—CH$_2$—, —CH$_2$—CH$_2$(CH$_2$)$_7$—CH$_3$); 2.35 (crude t, 2H, —CH$_2$CO$_2$Et); 2.68 (t, J=7 Hz, 2H, —CH$_2$(CH$_2$-

)8—CH3); 3.40 (dt, J=7 Hz, 2H, —NHCH2); 4.14 (q, J=7 Hz, 2H, —CO2CH2CH3); 7.23 (d, J=5 Hz, 1H, ring H5); 8.04 (s, 1H, ring H2); 8.09 (br s, 1H, —NH—); 8.41 (d, J=5 Hz, 1H, ring H6).

TLC: $R_f$ (silica gel, 1:9 MeOH/CH2Cl2)=0.59, UV, PMA.

Microanalysis Calcd for $C_{23}H_{38}N_2O_3$: C, 70.73; H, 9.82; N, 7.17. Found: C, 71.06; H, 9.96; N, 7.19.

EXAMPLE 8

5-[[(4-Decyl-2-pyridinyl)carbonyl]amino]pentanoic acid

A solution of 0.20 g (0.52 mmol) of 5-[[(4-decyl-2-pyridinyl)carbonyl]amino]pentanoic acid, ethyl ester prepared in Example 7, 0.05 g (1 mmol, 2 eq) of LiOH·H2O in 4 ml of THF and 1 ml of H2O was stirred at room temperature for 21 hours, then 1.5 eq of glacial acetic acid was added. The resulting solution was poured into H2O and extracted with Et2O. The organic layers were combined, poured into H2O and extracted with Et2O. The organic layers were combined, dried (Na2SO4) and concentrated in vacuo. Hexanes were added to the residue and the flask was cooled. The resulting white solid was collected, yielding 180 mg (97%) of title compound: m.p. 54°–56° C.

IR (KBr pellet) 3393 (broad), 3328, 2960, 2849, 1713, 1641, 1603, 1540, 1467 cm$^{-1}$.

270 MHz $^1$H NMR (CDCl3) δ 0.80 (crude t, 3H, —n—C9H18—CH3); δ 1.31 (m, 14H, —CH2(CH2)7—CH3); 1.75 (m, 6H, —CH2CH2—nC8H17, —NHCH2(CH2)2CH2—); 2.44 (crude t, J=6 Hz, 2H, —CH2CO2H); 2.65 (t, J=6 Hz, 2H, —CH2—nC9H19); 3.48 (m, 2H, —NHCH2—); 7.22 (d, J=6 Hz, 1H, ring H5); 8.24 (s, 1H, ring H3); 8.38 (br s, 1H, —NH—); 8.71 (d, J=6 Hz, 1H, ring H6); 10.62 (br s, 1H, —CO2H).

TLC: $R_f$ (silica gel, 1:9 MeOH/CH2Cl2)=0.34, U.V.

Microanalysis calcd for $C_{21}H_{34}N_2O_3$: C, 69.59; H, 9.45; N, 7.73. Found: C, 69.42; H, 9.52; N, 7.34.

EXAMPLE 9

3-[[(5-Decyl-2-pyridinyl)carbonyl]amino]propionic acid, ethyl ester

A. 3-(1-Decenyl)pyridine

To a solution of 43.1 g (91.9 mM) of Wittig salt 1-triphenylphosphononyl bromide in 500 ml of dry THF cooled to −78° was added dropwise 35 ml (2.6M in hexane, 91 mm) of n-butyllithium solution over 15 minutes. The reaction mixture was stirred at −78° for 1.5 hours then 8.0 ml (85 mm) of 3-pyridinecarboxaldehyde was added dropwise. After 15 minutes the reaction mixture was allowed to warm to 0° over 2 hours and then was stirred at 0° for 1 hour. The resulting dark solution was quenched with 5 ml of H2O and concentrated in vacuo. The residue was added to 150 ml of H2O overlaid with 150 ml of petroleum ether. The insoluble solids were removed by filtration, the organic layer was separated from the filtrate and the aqueous layer extracted with 50 ml of petroleum ether. The combined organic extracts were dried (MgSO4), concentrated in vacuo and purified by flash chromatography (15×10 cm, silica gel, 2:3 EtOAc/petroleum ether) to afford 15.1 g (82%) of title olefin as a yellow liquid.

IR (film) 3.42, 6.41, 6.90, 7.10, 9.83, 12.25, 14.15μ.

60 MHz $^1$H NMR (CDCl3) δ 0.57–1.93 (broad, 15H); 2.0–2.60 (m, 2H); 5.77 (dt, J=7, 12, 1H); 6.35 (d, J=12, 1H); 7.00–7.38 (m, 1H); 7.40–7.73 (m, 1H); 8.30–8.63 (m, 2H).

TLC: $R_f$ (silica gel, 1:1 EtOAc/petroleum ether)=0.36, trans isomer and 0.51, cis isomer, UV and PMA.

The 270 MHz $^1$H NMR (CDCl3) spectrum of title compound indicated the cis/trans mixture was ∼85:15.

B. 3-n-Decylpyridine

A mixture of 15.0 g (69.1 mM) of Part A olefin, 1.0 g of 10% Pd/C catalyst and 2 ml of glacial HOAc in 50 ml of sieve-dried methanol was shaken under an atmosphere of hydrogen (Paar apparatus) for 12 hours. The reaction mixture was filtered through Celite and the filtrate concentrated by roto-evaporation, then overnight under oil pump vacuum to afford 14.5 g (96%) of 3-n-decylpyridine as a yellow liquid.

IR (film) 3.43, 6.34, 6.89, 7.05, 9.83, 12.75, 14.14μ.

60 MHz $^1$H NMR (CDCl3) δ 0.45–2.00 (broad, 19H); 2.60 (t, J=7, 2H); 7.00–7.62 (m, 2H); 8.50 (m, 2H).

MS(Cl): 220 (M+H$^+$)

TLC: $R_f$ (silica gel, 1:1 EtOAc/petroleum ether)=0.42, UV, overlaps with cis-2.

C. 3-n-Decylpyridine-N-oxide

To a slurry of 14.5 g (85%, 71 mM) of meta-chloroperbenzoic acid in 100 ml of reagent CH2Cl2 cooled to 0° was added 14.2 g (64.8 mM) of Part A compound in one portion. The reaction mixture was warmed to room temperature and after 2 hours filtered through a column of 300 g of basic alumina (activity I, 1:9 MeOH/CH2Cl2 elution). The filtrate was concentrated in vacuo to afford 14.2 g (93%) of title N-oxide as an oily solid.

IR (film) 3.42, 6.21, 7.00, 7.90, 8.69, 9.91, 12.70, 13.22, 14.84.

60 MHz $^1$H NMR (CDCl3) δ 0.62–1.95 (broad, 19H); 2.58 (crude t, J=7, 2H); 7.00–7.35 (m, 2H); 8.08 (m, 2H).

TLC: $R_f$ (silica gel, 1:9 MeOH/CH2Cl2)=0.34, UV. The $R_f$ of Part B compound under identical conditions was 0.52.

D. 2-Cyano-5-n-decylpyridine and

E. 2-Cyano-3-n-decylpyridine

A solution of 14.2 g (60.4 mM) of Part C N-oxide, 35 ml (250 mM) of sieve-dried triethylamine and 27 ml (200 mM) of trimethylsilylcyanide in 50 ml of sieve-dried acetonitrile was refluxed (bath temperature 100°) for 20 hours. The dark reaction mixture was cooled in an ice-bath, quenched with 5 ml of H2O then added to 250 ml of H2O and extracted with two 75 ml portions of petroleum ether. The combined organic extracts were washed with three 200 ml portions of H2O, percolated through Na2SO4, dried (MgSO4) and concentrated in vacuo to give a dark oil. The crude oil was purified by flash chromatography (22×10 cm, silica gel, 1:12 EtOAc/petroleum ether) to afford 4.62 g (31%) of title D nitrile as a low melting orange solid and 7.94 g (54%) of title E nitrile as a pale yellow solid, mp 44°–45°.

Characterization of title D nitrile:

IR (film) 3.44, 4.44, 6.22, 6.38, 6.83, 7.23, 7.79, 8.91, 9.82, 11.82, 12.03, 13.23, 13.98μ.

270 MHz $^1$H NMR (CDCl3) δ 0.88 (t, J=7, 3H); 1.10–1.48 (broad m, 14H); 1.63 (m, 2H); 2.70 (t, J=7, 2H); 7.63 (s, 2H); 8.54 (s, 1H).

Partial 67.5 MHz $^{13}$C NMR (CDCl$_3$) δ 117.40(w), 128.06, 131.27(w), 136.40, 142.37, 151.41.

TLC: R$_f$ (silica gel, 1:9 EtOAc/petroleum ether)=0.23, UV.

Characterization of title E nitrile:

IR (KBr) 3.43, 4.48, 6.40, 6.80, 7.03, 8.91, 12.50μ.

270 MHz $^1$H NMR (CDCl$_3$) δ 0.88 (t, J=7, 3H); 1.05–1.50 (broad, 14H); 1.68 (m, 2H); 2.86 (t, J=7, 2H); 7.43 (dd, J=4, 9, 1H); 7.67 (d, J=9, 1H); 8.53 (d, J=4, 1H);

Partial 67.5 MHz $^{13}$C NMR (CDCl$_3$) δ 116.3(w), 126.55, 133.72(w), 137.15, 143.09(w), 148.42.

TLC: R$_f$ (silica gel, 1:9 EtOAc/petroleum ether)=0.14, UV.

F. 5-Decyl-2-pyridinecarboxylic acid

A solution of 3.00 g (12.3 mM) of Part D nitrile in 7.0 ml of ethanol and 7.0 ml of 10N aqueous NaOH was refluxed for 2.5 hours. The reaction mixture was cooled, added to b 50 ml of 20% aqueous HOAc and extracted with 25 ml of warm ethyl acetate. The organic layer was dried (MgSO$_4$), and concentrated in vacuo to give a solid. The crude material was washed with 1:1 ether/petroleum ether on a Büchner funnel. Recrystallization (aqueous MeOH) and drying under vacuum afforded 2.20 g (68%) of title acid as flaky, white plates, m.p. 104°–105°.

IR (KBr) 3.42 (broad), 5.89, 6.15, 6.31, 7.19, 7.67, 8.08, 8.86μ.

270 MHz $^1$H NMR (CDCl$_3$) δ 0.88 (t, J=7,3H); 1.05–1.48 (broad, 14H); 1.66 (m, 2H); 2.73 (t, J=7, 2H); 7.75 (dd, J=1, 8, 1H); 8.15 (d, J=8, 1H); 8.50 (s, 1H); 10.25 (broad, 1H).

Partial 67.5 MHz $^{13}$C NMR (CDCl$_3$) δ 123.68, 138.10, 143.32(w), 144.24(w), 148.06, 164.46(w).

MS (CI): 264 (M+H$^+$).

TLC: R$_f$ (silica gel, 1:1:8 HOAc/MeOH/CH$_2$Cl$_2$)=0.40 (tails), UV

Microanalysis Calcd for C$_{16}$H$_{25}$NO$_2$: C, 72.96; H, 9.57; N, 5.32. Found: C, 72.73; H, 9.46; N, 5.20.

G. 3-[[(5-Decyl-2-pyridinyl)carbonyl]amino]propionic acid, ethyl ester

To a solution of 500 mg (1.90 mmol) of Part F pyridyl acid in 8.0 ml of dry CH$_2$Cl$_2$ at 0° was added 0.32 ml (2.2 mmol) of diethyl chlorophosphate, then 0.32 ml (2.3 mmol) of sieve-dried triethylamine. The reaction mixture was warmed to room temperature, stirred for 1 hour then 380 mg (2.48 mmol) of β-alanine ethyl ester hydrochloride was added followed by 0.35 ml (2.5 mmol) of triethylamine. After 1 hour the resulting slurry was filtered through a short column of 25 g of basic alumina (activity I) eluting with several column volumes of ethyl acetate. The filtrate was concentrated in vacuo and the residual crude oil was purified by flash chromatography (12×3.0 cm, silica gel, 1:2 EtOAc/petroleum ether) to afford 375 mg (55%) of title ether as a pale yellow oil.

IR (CCl$_4$) 3.42, 5.76, 5.96, 6.60, 6.79, 7.29, 8.43, 9.76μ.

270 MHz $^1$H NMR (CDCl$_3$) δ 0.88 (t, J=8, 3H); 1.10–1.45 (m, 19H); 1.62 (m, 2H); 2.64 (t, J=7, 2H); 3.75 (dt, J=7, 7, 2H);

4.18 (q, J=7, 2H);

7.62 (dd, J=2, 8, 1H);

8.08 (d, J=8, 1H);

8.36 (d, J=2, 1H);

8.40 (broad s, 1H).

Partial 67.5 MHz $^{13}$C NMR(δ) 121.83, 136.87, 141.11(w), 148.34, 164.60(w), 172.19(w).

MS(CI): 363 (M+H$^+$).

TLC: R$_f$ (silica gel, 1:2 EtOAc/pet ether)=0.29, PMA and UV.

Microanalysis Calcd for C$_{21}$H$_{34}$N$_2$O$_3$: C, 69.58; H, 9.45; N, 7.73. Found: C, 69.08; H, 9.68; N, 7.68.

EXAMPLE 10

3-[[(5-Decyl-2-pyridinyl)carbonyl]amino]propionic acid

A mixture of 220 mg (0.61 mmol) of Example 9 ester and 75 mg (1.8 mmol) of lithium hydroxide monohydrate in 5 ml of 4:1 THF/H$_2$O was stirred rapidly at room temperature for 2 hours; then 0.10 ml (1.7 mmol) of glacial acetic acid was added. The resulting solution was added to 20 ml of H$_2$O and extracted with two 20 ml portions of ethyl acetate. The combined organic extracts were dried (MgSO$_4$) and concentrated in vacuo to give a white solid. Recrystallization (ether/petroleum ether) and drying under vacuum afforded 156 mg (77%) of title acid as small white crystals, m.p. 93°–94°.

IR (KBr) 2.96, 3.43 (broad), 5.79, 6.09, 6.53, 6.78, 6.85, 8.46, 11.66, 14.55μ.

270 MHz $^1$H NMR (CDCl$_3$) δ 0.88 (t, J=7, 3H); 1.10–1.45 (broad s, 14H); 1.62 (m, 2H); 2.65 (t, J=8, 2H); 2.73 (t, J=6, 6, 2H); 3.78 (dt, J=6, 6, 2H); 7.64 (dd, J=2, 8, 1H); 8.10 (d, J=8, 1H); 8.35 (d, J=2, 1H); 8.46 (crude t, J~6, 1H).

Partial 67.5 MHz $^{13}$C NMR (CDCl$_3$) δ 122.36, 137.23, 141.45(w), 147.39(w), 148.17, 164.83(w), 176.24(w).

MS (CI): 335 (M+H$^+$), 317 (M+H$^+$—H$_2$O)

TLC: R$_f$(silica gel, 1:9 MeOH/CH$_2$Cl$_2$)=0.33, PMA and UV.

Microanalysis Calcd for C$_{19}$H$_{30}$N$_2$O$_3$: C, 68.23; H, 9.04; N, 8.38. Found: C, 68.05; H, 8.88, N, 8.12.

EXAMPLE 11

4-[[(5-Decyl-2-pyridinyl)carbonyl]amino]butanoic acid, ethyl ester

To a solution of 600 mg (2.41 mmol) of 5-decyl-2-pyridinecarboxylic acid (prepared in Example 9 Parts A to F) in 10 ml of dry CH$_2$Cl$_2$ cooled to 0° was added 0.40 ml (2.7 mmol) of diethyl chlorophosphate, then 0.40 ml (2.8 mmol) of triethylamine. The reaction mixture was warmed to room temperature and after 1 hour 480 mg (2.86 mmol) of powdered ethyl 4-aminobutyrate hydrochloride was added followed by 0.42 ml (3.0 mmol) of triethylamine. The reaction mixture was stirred for 1.5 hours then the resulting slurry was filtered through a short column of 25 g of basic alumina (activity I) eluting with several column volumes of ethyl acetate. The filtrate was concentrated in vacuo and the resulting crude oil was purified by flash chromatography (12×3.0 cm, silica gel, 1:3 EtOAc/petroleum ether) to afford 680 mg (75%) of title ester as a pale yellow oil, which solidified upon cooling.

IR (CHCl$_3$) 3.42, 5.79, 6.00, 6.54, 6.79, 9.75μ.

270 MHz $^1$H NMR (CDCl$_3$) δ 0.88 (t, J=7, 3H); 1.05–1.45 (broad, 18H); 1.62 (m, 2H); 1.98 (tt, J=7, 7, 2H); 2.41 (t, J=7, 2H); 2.68 (t, J=7, 2H); 3.53 (dt, J=7, 7, 2H); 4.11 (q, J=7, 2H); 7.62 (dd, J=2, 8, 1H); 8.09 (d, J=8 with broad—NH singlet at 8.07, 2H total); 8.35 (d, J=2, 1H).

Partial 67.5 MHz $^{13}$C NMR (CDCl$_3$) δ 121.86, 136.93, 141.08(w), 147.70(w), 148.20, 164.63(w), 173.09(w).

MS(CI): 377 (M+H+).

TLC: $R_f$ (silica gel, 1:2 EtOAc/petroleum ether)=0.37, PMA and UV.

Microanalysis Calcd for $C_{22}H_{36}N_2O_3$: C, 70.18; H, 9.64; N, 7.44. Found: C, 70.25; H, 9.76; N, 7.39.

EXAMPLE 12

4-[[(5-Decyl-2-pyridinyl)carbonyl]amino]butanoic acid

A solution of 520 mg (1.38 mmol) of Example 11 ester and 168 mg (4.00 mmol) of lithium hydroxide monohydrate in 7 ml of 5:2 THF/H$_2$O was stirred rapidly at room temperature for 16 hours. The resulting solution was acidified with 0.35 ml (6.0 mmol) of glacial HOAc, added to 25 ml of H$_2$O and extracted with two 20 ml portions of ethyl acetate. The combined organic extracts were dried (MgSO$_4$), concentrated in vacuo to give an oil. The crude material was filtered through a short column of silica gel (1:9 MeOH/CH$_2$Cl$_2$ elution) and the filtrate concentrated in vacuo to give an oil which solidified upon cooling. Recrystallization (ether/petroleum ether) and drying under vacuum afforded 425 mg (88%) of title acid as a microcrystalline white solid, m.p. 42°–43°.

IR(KBr) 2.98 (broad) 3.42, 5.90, 6.05, 6.55, 6.82, 6.92, 8.07.

400 MHz $^1$H NMR (CDCl$_3$) δ 0.88 ppm (t, J=7, 3H); 1.13–1.38 (broad s, 14H); 1.63 (m, 2H); 2.00 (tt, J=7.7, 2H); 2.47 (t, J=7, 2H); 2.67 (t, J=8, 2H); 3.57 (dt, J=7, 7, 2H); 7.65 (dd, J=2, 8, 1H); 8.10 (d, J=8, 1H); 8.22 (crude t, J=6, 1H); 8.36 (s, 1H).

TLC: $R_f$(silica gel, 1:9 MeOH/CH$_2$Cl$_2$)=0.46, UV.

Microanalysis calcd for $C_{20}H_{32}N_2O_3$: C, 68.93; H, 9.26; N, 8.04. Found: C, 69.09; H, 9.17; N, 8.04.

EXAMPLE 13

4-[[(5-Decyl-2-pyridinyl)carbonyl]amino]pentanoic acid, ethyl ester

A. Ethyl-5-aminovalerate hydrochloride

Hydrogen chloride was bubbled into 100 ml of dry ethanol (sieve-dried) cooled in an ice bath until saturated then 25.0 g (214 mmol) of 5-aminovaleric acid was added. The resulting slurry was warmed to room temperature and stirred for 18 hours. Argon was bubbled into the reaction mixture for several hours to remove excess HCl and the resulting solution concentrated in vacuo to ~½ volume. The slurry which formed was warmed until homogeneous, 200 ml of ether was added and the solution cooled overnight in refrigerator. The crystals which formed were collected on a Büchner funnel, washed several times with ether and dried under vacuum to afford 32.3 gr (83%) of title compound as flaky, white plates, m.p. 109°–110°.

60 MHz $^1$H NMR (CDCl$_3$) δ 1.25 (t, J=7, 3H); δ1.55–2.20 (broad, 4H); 2.37 (m, 2H); 3.07 (broad, 2H); 4.12 (q, J=7, 2H); 8.25 (broad, 3H);

TLC: $R_f$ (silica gel, 1:2:8 HOAc/MeOH/CH$_2$Cl$_2$)=0.33, ninhydrin

B. 4-[[(5-Decyl-2-pyridinyl)carbonyl]amino]pentanoic acid, ethyl ester

To a solution of 520 mg (1.98 mmol) of 5-decyl-2-pyridinecarboxylic acid (prepared in Example 9) in 8.0 ml of dry CH$_2$Cl$_2$ cooled to 0° was added 0.35 ml (2.4 mmol) of diethyl chlorophosphonate then 0.35 ml (2.5 mmol) of triethylamine. The reaction mixture was warmed to room temperature and after 1 hour 450 mg (2.48 mmol) of ethyl 5aminovalerate hydrochloride, was added followed by 0.35 ml (2.5 mmol) of triethylamine. The reaction mixture was stirred for an additional 1 hour and the resulting slurry filtered through a short column of 25 g of basic alumina (activity I) eluting with several column volumes of ethyl acetate. The filtrate was concentrated in vacuo to give a crude yellow oil. The crude material was purified by flash chromatography (15×3.0 cm, silica gel, 1:3 EtOAc/petroleum ether) to afford 550 mg (71%) of title ester as a pale yellow oil.

IR (CCl$_4$) 3.42, 5.76, 5.96, 6.57, 6.79, 7.27μ.

270 MHz $^1$H NMR (CDCl$_3$) δ 0.88 (t, J=7, 3H); δ1.12–1.43 (m, 17H); 1.52–1.85 (m, 6H); 2.35 (t, J=7, 2H); 2.66 (t, J=8, 2H); 3.48 (dt, J=7, 7, 2H); 4.13 (q, J=7, 2H); 7.62 (dd, J=2, 8, 1H); 8.03 (crude t, 1H); 8.09 (d, J=8, 1H); 8.34 (d, J=2, 1H).

Partial 67.5 MHz $^{13}$C NMR (CDCl$_3$) δ 121.83, 136.93, 141.00(w), 147.75(w), 148.14, 164.49(w), 173.34(w).

MS (CI): 391 (M+H+).

TLC: $R_f$ (silica gel, 1:2 EtOAc/petroleum ether)=0.42, UV and PMA.

Microanalysis calcd for $C_{23}H_{38}N_2O_3$: C, 70.73; H, 9.81, N, 7.17. Found: C, 70.60; H, 9.75; N, 6.99.

EXAMPLE 14

4-[[(5-Decyl-2-pyridinyl)carbonyl]amino]pentanoic acid

A mixture of 305 mg (0.78 mmol) of Example 13 ester and 100 mg (2.38 mmol) of lithium hydroxide monohydrate in 5 ml of 4:1 THF/H$_2$O was stirred rapidly for 20 hours, then 0.20 ml (3.0 mmol) of glacial HOAc was added. The reaction mixture was added to 20 ml of H$_2$O and extracted with two 15 ml portions of ether. The combined ether extracts were dried (MgSO$_4$) and concentrated in vacuo to give a white solid. Recrystallization (ether/petroleum ether) and drying under vacuum afforded 243 mg (86%) of title acid as feathery, white crystals, m.p. 49°–51°.

IR (KBr) 3.02, 3.43 (broad), 5.87, 6.10, 6.55, 6.80, 6.99, 7.94, 8.32μ.

270 MHz $^1$H NMR (CDCl$_3$) δ 0.88 (t, J=7, 3H); δ 1.10–1.45 (broad, 14H); 1.50–1.88 (m, 6H); 2.42 (t, J=7, 2H); 2.66 (t, J=8, 2H); 3.50 (dt, J=7, 7, 2H); 7.63 (dd, J=2, 8, 1H); 8.11 (d, J=8, with overlapping –NH broad s, 2H); 8.34 (d, J=2, 1H).

Partial 67.5 MHz $^{13}$C NMR (CDCl$_3$) δ 122.14, 137.12, 141.20, 147.64(w), 148.12, 164.66(w), 178.02(w).

MS(CI): 363 (M+H+).

TLC: $R_f$(silica gel, 1:9 MeOH/CH$_2$Cl$_2$)=0.51, PMA and UV.

Microanalysis calcd for $C_{21}H_{34}N_2O_3$: C, 69.58; H, 9.45; N, 7.73. Found: C, 69.83; H, 9.51; N, 7.65.

EXAMPLE 15

4-[[(5-(1-Tridecenyl-2-pyridinyl)carbonyl]amino]butanoic acid

A. 1-Triphenylphosphododecyl bromide

A solution of 10.0 g (0.040 mmol) of 1-bromododecane and 13.1 g (0.050 mmol, 1.2 eq) of triphenylphosphine was heated to ~120° C. for 4 hours, then cooled to room temperature. To this was added Et$_2$O and the mixture was stirred and decanted. This washing procedure was repeated 3 times. The resulting residue was dissolved in CH$_2$Cl$_2$ and Et$_2$O was added until the solution remained cloudy. The flask was cooled until 2 layers separated; the Et$_2$O layer was decanted and the CH$_2$Cl$_2$ layer was concentrated in vacuo. This procedure was repeated 3 times to yield 15.6 g (75%) of title bromide as a light yellow foam.

IR (CDCl$_3$): δ 1.24 (br m, 23H, CH$_3$(CH$_2$)$_{10}$—CH$_2$) 3.73 (br s, 2H, CH$_3$(CH$_2$)$_{10}$—CH$_2$—) 7.90 (s, 15H, aromatic H's).

TLC: R$_f$ (1:9 MeOH/CH$_2$Cl$_2$)=0.29, UV, PMA.

B. 3-(1-Tridecenyl)pyridine

A solution of 15.5 g (30 mmol, 1 eq) of Part A bromide in 130 ml of dry THF was cooled to −78° C. and 15.8 ml (33 mmol, 1.1 eq., 2.1M in hexane) of n-BuLi was added dropwise. This was followed by the dropwise addition of 36.5 ml (210 mmol, 7 eq) of HMPA. The solution was stirred for 30 minutes. A solution of 3.0 g (30 mmol) of 3-pyridinecarboxaldehyde in 64 ml of THF was added. The resulting solution was warmed to room temperature and stirred for 2.25 hours. Water was added to the reaction and this was extracted with Et$_2$O. The organic layers were combined, washed with saturated NH$_4$Cl, followed by saturated NaCl and dried (Na$_2$SO$_4$). The solution was filtered and concentrated in vacuo. Hexanes were added to the residue; the supernatant was decanted from the solids and concentrated in vacuo. The crude material was purified by flash chromatography (15×3 cm, silica gel, 1:5 EtOAc/petroleum ether) to yield 4.1 g (53%) of title pyridine compound as a yellow oil.

IR (film) 3011, 2928, 1585, 1564, 1465 cm$^{-1}$.

270 MHz $^1$H NMR (CDCl$_3$) δ 0.87 (t, 3H, —(CH$_2$)$_{10}$CH$_3$); δ 1.36 (br m, 18H, —CH$_2$(CH$_2$)$_9$CH$_3$); 2.28 (dt, J=6, 7 Hz, 2H, —CH$_2$—nC$_{10}$H$_{21}$); 6.34 (dt, J=7, 11 Hz, 1H, —CH=CH—nC$_{11}$H$_{23}$); 6.80 (d, J=11 Hz, 1H, —CH=CH—nC$_{11}$H$_{23}$); 7.45 (dd, J=5, 8 Hz, 1H, ring H$_5$); 7.56 (d, J=8 Hz, 1H, ring H$_4$); 8.44 (d, J=5 Hz, 1H, ring H$_6$); 8.52 (s, 1H, ring H$_2$).

Partial 270 MHz $^{13}$C NMR (CDCl$_3$): 149.84 (ring C$_2$), 147.36 (ring C$_6$), 135.7 (—HC=CH—), 133.44 (ring C$_3$) 125.09 (ring C$_5$), 123.00 (ring C$_4$).

TLC: R$_f$ (1:1 EtOAc/petroleum ether)=0.50 UV, PMA.

C. 3-(1-Tridecenyl)pyridine-N-oxide

A solution of 3.8 g (15 mmol) of Part A pyridine compound in 20 ml of distilled toluene was cooled to −78° C. and 2.8 g (14.7 mmol, 1 eq) of meta-chloroperbenzoic acid in 80 ml of distilled toluene and 100 ml of chloroform was added. The solution was stirred at room temperature for 24 hours. The reaction mixture was concentrated in vacuo and placed on a column of basic alumina (activity I), then eluted with CHCl$_3$, followed by 1:3 MeOH/CHCl$_3$. The MeOH/CHCl$_3$ fraction was concentrated in vacuo and purified via flash chromatography (25×9 cm, silica gel, 1:1 EtOAc/petroleum ether, 1 liter, 1:15 MeOH/CH$_2$Cl$_2$, 1.6 liters) to give 3.3 g (80%) of title N-oxide as a white solid: m.p. 58°-60° C.

IR(KBr Pellet) 3432, 3053, 2917, 2856, 1593, 1482, 1468, 1462, 1441, 1286, 1012, 808 cm$^{-1}$.

270 MHz $^1$H NMR (CDCl$_3$): δ 0.88 (t, 3H, —(CH$_2$)$_{10}$(CH$_3$); δ 1.27 (br s, 16H, (CH$_2$)$_2$—(CH$_2$)$_8$CH$_3$); 1.44 (crude t, 2H, CH$_2$—CH$_2$—nC$_9$H$_{19}$); 2.25 (dt, J=6, 7 Hz, 2H, —CH$_2$—nC$_{10}$H$_{21}$); 5.90 (dt, J=7, 11 Hz, 1H, —HC=CH—CH$_2$—); 6.22 (d, J=7 Hz, 1H, —HC=CH—CH$_2$); 7.13 (d, J=8 Hz, 1H, ring H$_4$); 7.20 (dd, J=7, 8 Hz, 1H, ring H$_5$); 8.08 (d, J=7 Hz, 1H, ring H$_6$); 8.15 (s, 1H, ring H$_2$).

TLC: R$_f$ (1:9 MeOH/CH$_2$Cl$_2$)=0.44, UV, PMA

D. 2-Cyano-3-tridecenylpyridine and

E. 2-Cyano-5-tridecenylpyridine

To a solution of 3.0 g (11 mmol) of Part C N-oxide in 75 ml of dry CH$_3$CN was added 4.5 ml (33 mmol, 3 eq) of triethylamine. The solution was stirred at room temperature and 7.3 ml (55 mmol, 5 eq) of trimethylsilyl cyanide was added dropwise. The reaction was heated to 100° C. for 16 hours and then cooled to room temperature. To this was added H$_2$O and the mixture was extracted with Et$_2$O. The organic layer was washed with 1N NaOH, dried (Na$_2$SO$_4$) and finally concentrated in vacuo. Purification of the crude material was accomplished via flash chromatography (25×9 cm, silica gel, 1:15 EtOAc/petroleum ether) to yield 1.4 g (46%) of title D nitrile as a white solid: m.p. 48°-49° C., and 1.3 g (42%) of title E nitrile as a white solid.

IR (KBr Pellet) of title D nitrile: 3435, 2956, 2916, 2851, 2231, 1553, 1468, 1425, 1395, 1095, cm$^{-1}$.

270 MHz $^1$H NMR (CDCl$_3$) of title D nitrile δ 0.87 (t, 3H, —(CH$_2$)$_8$CH$_3$); 1.24 (br s, 16H, —(CH$_2$)$_8$CH$_3$); 2.22 (dt, J=6, 7 Hz, 2H, —CH$_2$—nC$_{10}$H$_{21}$); 6.05 (dt, J=7, 12 Hz, 1H, —CH=CH—CH$_2$); 6.58 (d, J=12 Hz, 1H, —CH=CH—CH$_2$); 7.46 (dd, J=4, 8 Hz, 1H, ring H$_5$); 7.74 (d, J=8 Hz, 1H, ring H$_4$); 8.56 (d, J=4 Hz, 1H, ring H$_6$);

TLC: R$_f$ (1:9 EtOAc/petroleum ether)=0.23, UV, PMA.

IR(KBr Pellet) of title E nitrile: 3441, 3052, 3015, 2914, 2849, 2235, 1469, 1365 cm$^{-1}$.

270 MHz $^1$H NMR (CDCl$_3$) of title E nitrile: δ 0.90 (t, 3H, —(CH$_2$)$_{10}$CH$_3$); 1.27 (br s, 16H, —(CH$_2$)$_8$CH$_3$); 1.47 (m, 2H, —CH$_2$CH$_2$)—nC$_9$H$_{19}$); 2.29 (dt, J=6, 7 Hz, 2H, —CH$_2$—nC$_{10}$H$_{21}$); 5.96 (dt, J=7, 11 Hz, 1H, HC=CH—CH$_2$); 6.37 (d, J=11 Hz, 1H, HC=CH—CH$_2$); 7.48 (m, 2H, ring H$_3$ and ring H$_4$); 8.61 (s, 1H, ring H$_6$).

TLC: R$_f$ (1:9 EtOAc/petroleum ether)=0.33, UV, PMA.

F. (cis)-5-(1-Tridecenyl)-2-pyridinecarboxylic acid

A solution of 0.40 g (1.4 mmol) of Part E nitrile in 25 ml of 10N NaOH and 25 ml of EtOH was refluxed for 2 hours. The reaction was cooled and 11.5 ml (1 eq) of glacial acetic acid was added. The reaction was filtered and the solid was dissolved in 1N HCl and extracted with CH$_2$Cl$_2$. The organic extract was dried (Na$_2$SO$_4$) and concentrated in vacuo. The crude solid was recrystallized with petroleum ether to yield 0.31 g (73%) of title acid as a white solid: m.p. 68°-69° C.

IR(KBr Pellet) 3429, 2921, 2851, 1696, 1467 cm$^{-1}$.

270 MHz $^1$H NMR (CDCl$_3$): δ 0.87 (t, 3H, (CH$_2$)$_{10}$CH$_3$); δ 1.17 (br s, 16H, —(CH$_2$)$_2$(CH$_2$)$_8$CH$_3$); 1.47 (m, 2H, —CH$_2$CH$_2$—nC$_9$H$_{19}$); 2.32 (dt, J=6, 7 Hz, 2H, —CH$_2$—nC$_{10}$H$_{21}$); 5.97 (dt, J=7, 11 Hz, 1H, HC=CH—CH$_2$); 6.45 (d, J=11 Hz, 1H, HC=CH—CH$_2$—); 7.81 (d, J=7 Hz, 1H, ring H$_4$); 8.19 (d, J=7 Hz, 1H, ring H$_3$); 8.58 (s, 1H, ring H$_6$); 10.76 (br s, 1H, —CH$_2$H).

Partial 270 MHz $^{13}$H NMR (CDCl$_3$): 164.39 (ring C$_6$), 148.17 (ring C$_2$), 143.87 (ring C$_3$), 138.57 (ringC$_5$), 137.90 (ring C$_4$), 124.03 (HC=CH), 123.48 (HC=CH).

MS(CI): 304 (M+H)$^+$.

TLC: R$_f$ (1:9 MeOH/CH$_2$Cl$_2$)=0.16, Tails, UV, PMA.

Microanalysis Calcd for $C_{19}H_{29}NO_2$: C, 75.21; H, 9.63; N, 4.62. Found: C, 74.89; H, 9.77; N, 4.55.

G.
4-[[[5-(1-Tridecenyl)-2-pyridinyl]carbonyl]amino]-butanoic acid, ethyl ester To a solution of 88 mg (0.29 mmol) of Part F acid in 4 ml of dry $CH_2Cl_2$ at 0° was added 46 ml (0.32 mmol) of diethyl chlorophosphate then 46 ml (0.33 mmol) of sieve-dried triethylamine. The reaction mixture was warmed to room temperature, stirred for 1 hour then an additional 0.46 ml (0.33 mmol) of triethylamine was added followed by 60 mg (0.36 mmol) of ethyl-4-aminobutyrate hydrochloride. The resulting solution was stirred for 2.5 hours then filtered through a small column of basic alumina (7×1 cm, activity I) eluting with ethyl acetate. The eluant was concentrated in vacuo to afford 84 mg (70%) of crude title ester as an oil.

60 MHz $^1H$ NMR ($CDCl_3$) δ 0.60–2.70 (m, 30H); δ 3.53 (dt, J=6,6,2H, —NH—$CH_2$—); 4.12 (q, J=7, 2H, —$CO_2CH_2CH_3$); 5.87 (dt, J=7, 12, 1H, olefinic); 6.45 (d, J=12, 1H, olefinic); 7.73 (dd, J=2,8,1H, ring $H_4$); 8.17 (d with broad —NH— singlet underneath, J for d=8, 2H, ring $H_3$ and —NH—); 8.47 (d, J=2, 1H, ring $H_6$).

TLC: $R_f$ (silica gel, 1:4 EtOAc/petroleum ether)=0.18, UV and PMA.

H.
4-[[[5-(1-Tridecenyl)-2-pyridinyl]carbonyl]amino]-butanoic acid

A mixture of 84 mg (0.20 mmol) of Part G ester and 30 mg (0.71 mmol) of lithium hydroxide monohydrate in 2.5 ml of 1:4 $H_2O$/THF was stirred for 16 hours at room temperature. The reaction mixture was added to 10 ml of 0.1M aqueous HCl solution and extracted with 10 ml of ethyl acetate. The organic extract was dried (MgSO$_4$) and concentrated in vacuo to afford 68 mg (90%) of crude title acid as a solid, m.p. 53°–54°.

60 MHz $^1H$ NMR ($CDCl_3$) δ 0.60–2.75 (m, 27H); δ 3.55 (dt, J=7,7,2H, —NH—$CH_2$—$CH_2$—); 5.88 (dt, H=7,12,1H, olefinic); 6.40 (d, J=12, 1H, olefinic); 7.68 (dd, J=2,8,1H, ring $H_4$);8.13 (d with broad —NH— singlet underneath, J for d=8, 2H, ring $H_2$ and —NH—); 8.43 (br s, 1H, ring $H_6$); 9.77 (br s, 1H, —$CO_2H$);

TLC: $R_f$ (silica gel, 1:9 MeOH/$CH_2Cl_2$)=0.78, UV and PMA.

EXAMPLE 16
4-[[(5-Tridecyl-2-pyridinyl)carbonyl]amino]butanoic acid

A mixture of 67 mg (0.17 mmol) of 4-[[(5-(1-tridecenyl-2-pyridinyl)carbonyl]amino]butanoic acid (prepared as described in Example 15) and 20 mg of 10% palladium on charcoal catalyst in 5 ml of ethyl acetate was stirred rapidly under an atmosphere of hydrogen (balloon) for 2 hours. The resulting slurry was filtered through a short column (3×1 cm) of Celite to remove the catalyst. The filtrate was concentrated in vacuo to give a solid. Recrystallization (ether/petroleum ether) afforded 42 mg (65%) of title acid as a white, microcrystalline powder, m.p. 54°–55°.

IR (KBr) 3333, 2921, 1701, 1653, 1527, 1205 cm$^{-1}$.

270 MHz $^1H$ NMR ($CDCl_3$) δ 0.88 (t, J=7, 3H, —$CH_3$); δ 1.10–1.50 (m, 20H, —($CH_2$)$_{10}$—$CH_3$); 1.63 (m, 2H, —$CH_2(CH_2)_{10}$—$CH_3$); 1.99 (tt, J=7, 7, 2H, —$CH_2$—$CH_2$—$CO_2H$); 2.47 (t, J=7, 2H, —$CH_2CO_2H$); 2.66 (t, J=8, 2H, —$CH_2$—($CH_2$)$_{11}$—$CH_3$); 3.56 (dt, J=7, 2H, —NH—$CH_2$—); 7.64 (dd, J=2,8,1H, ring $H_4$); 8.10 (d, J=8, 1H, ring $H_3$); 8.21 (crude t, 1H, —NH—) 8.35 (d, J=2, 1H, ring $H_6$);

MS (CI): 391 (M+H)$^+$.

TLC: $R_f$(silica gel, 1:9 MeOH/$CH_2Cl_2$)=0.54, PMA and UV.

Analysis Calcd for $C_{23}H_{38}N_2O_3$: C, 70.73; H, 9.81; N, 7.17. Found: C, 70.68; H, 9.63; N, 7.08.

EXAMPLE 17
4-[[[5-(1-Decenyl)-2-pyridinyl]carbonyl]amino]-butanoic acid, ethyl ester

A. 3-(1-Decenyl)pyridine

A solution of 40 g (7.3 mmol) of 1-triphenylphosphononyl bromide dissolved in 20 ml of THF was cooled to −78° C. and 2.0 ml (2.6M in hexane, 5.2 mmol) of n-BuLi was added dropwise. This was followed by the dropwise addition of 4.5 ml (5.5. eq., 26 mmol) of HMPA. The solution was stirred for 5 minutes. Then a solution of 500 mg (4.70 mmol) of 3-pyridinecarboxaldehyde in 10 ml THF was added. The resulting solution was warmed to room temperature and stirred for 2 hours. Water was added to the reaction and this was extracted with $Et_2O$. The organic layer was washed with saturated $NH_4Cl$, followed by saturated NaCl and dried ($Na_2SO_4$). Hexanes were added to the resulting residue, decanted and concentrated. The crude material was purified by flash chromatography (9×3 cm, silica gel, 1:1 hexanes/EtOAc) to yield 777 mg (77%) of title pyridine as a yellow oil.

IR (film) 3005 (weak), 2940, 2880 (weak), 1575, 823, 795 cm$^{-1}$.

$^1H$ NMR ($CDCl_3$) δ 0.60–2.70 (br m, 17H); 5.74 (dt, J=12,6,1H); 6.34 (m, 1H); 7.14 (m, 1H); 7.50 (dt, J=2, 8 Hz, 1H); 8.50 (m, 2H).

$^{13}C$ NMR showed a single isomer.

TLC (1:1 hexanes/EtOAc) $R_f$=0.45, PMA, UV

B. 3-(1-Decenyl)pyridine-N-oxide

A solution containing 6.38 g (29.6 mmol) of title A pyridine in 23 ml of $CHCl_3$ was cooled to 0° C. and 5.88 g (29.6 mmol) of meta-chloroperbenzoic acid in 100 ml $CHCl_3$ was added. The temperature was maintained at 0° C. for 2.5 hours and then the reaction mixture was passed through a column of basic alumina, eluted with $CHCl_3$ followed by 1:3 MeOH/$CH_2Cl_2$. The MeOH/$CH_2Cl_2$ eluant was concentrated in vacuo and purified by flash chromatography (25×9 cm, silica gel, 1:19 MeOH/$CH_2Cl_2$) to give 5.42 g (80%) of N-oxide as a white hygroscopic solid: m.p. 29°–30° C.

IR (film) 3009 (weak), 3005, 2920, 2880, 1600, 1560, 798, 753 cm$^{-1}$.

$^1H$ NMR ($CDCl_3$) δ 0.60–2.58 (br m, 17H); 5.82 (dt, J=11, 6, 1H); 6.22 (d, J11 Hz, 1H); 7.20 (m, 2H); 8.10 (m, 2H).

TLC (1:9 MeOH/$CH_2Cl_2$), $R_f$=0.36, PMA.

C. 2-Cyano-5-decenylpyridine
and
D. 2-Cyano-3-decenylpyridine

To a solution of 3.50 g (15.1 mmol) of title B N-oxide in 80 ml of dry $CH_3CN$ was added 3.6 ml (26 mmol, 1.7 eq) of triethylamine. The solution was stirred at room temperature and 5.8 ml (43 mmol, 2.9 eq) of trimethylsilyl cyanide was added dropwise. The reaction was heated to 85° C. for 15 hours and subsequently cooled to room temperature. A solution of 1N NaOH was added and the solution was extracted with hexanes. The organic extracts were dried ($Na_2SO_4$), filtered and concentrated in vacuo. The crude material was purified by flash chromatography (15×3 cm, silica gel, 1:15 EtOAc/hexanes) to yield 1.31 g (36%) of title C nitrile as a white hygroscopic solid, m.p. 26°–28° C.; 1.46 g (40%) of title D nitrile as a clear oil.

IR (film) of title C nitrile: 3005 (weak), 2950, 2880, 2250, 1640, 1550, 1470, 1450, 815, 777 $cm^{-1}$.

$^1$H NMR ($CDCl_3$) of title C nitrile: δ 0.59–2.38 (br m, 17H); partial 270 MHz $^1$H NMR of vinyl and aromatic region δ 6.06 (dt, J=11,7, 1H); 6.70 (d, J=11 Hz, 1H); 7.46 (dd, J=2, 6, 1H); 7.75 (dd, J=2, 8, 1H); 8.58 (dd, J=2, 6, 1H).

TLC (1:2 EtOAc/hexanes) for title C nitrile, $R_f$=0.54, PMA, UV.

IR (film) of title D nitrile: 3003, 2930, 2850, 2250, 1590, 1560, 1460, 850 $cm^{-1}$.

$^1$H NMR ($CDCl_3$) for title D nitrile: δ 0.57–2.52 (br m, 17H); partial 270 MHz $^1$H NMR of vinyl and aromatic region, δ 5.98 (dt, J=11, 7, 1H); 6.38 (d, J=11 Hz, 1H); 7.60 (m, 2H); 8.61 (s, 1H).

TLC (1:2 EtOAc/hexanes) $R_f$=0.60, PMA, UV.

E. 5-(1-Decenyl)-2-pyridinecarboxylic acid

A solution of 1.30 g (5.38 mmol) of the Example 17 Part D nitrile, 30 ml of EtOH and 30 ml of 10N NaOH was refluxed for 2.5 hours. The reaction was cooled in an ice bath and acidified to pH 1 with concentrated HCl. The resulting slurry was filtered and the filtrate was concentrated in vacuo. Chloroform was added to the residue and filtered. The filtrate was concentrated in vacuo and purified by flash chromatography (9×3 cm, silica gel, MeOH 200 ml, 1:9 MeOH/$CH_2Cl_2$ 1000 ml) to yield title acid as a pale yellow solid, 510 mg (36%); m.p. 55°–57° C.

IR(KBr) 3430, 3013, 2956, 2923, 2520, 1696, 1592, 1565, 1467, 1433 $cm^{-1}$.

270 MHz $^1$H NMR ($CDCl_3$) δ 0.83 (m, 3H); 1.28 (m, 13H); 2.31 (m, 2H); 5.97 (m, 1H); 6.40 (d, J=11 Hz, 1H); 7.80 (d, J=9 Hz, 1H); 8.35 (d, J=9 Hz, 1H); 9.00 (s, 1H).

TLC (1:3 MeOH/$CH_2Cl_2$) $R_f$=0.65, PMA, UV.

F.
4-[[[5-(1-Decenyl)-2-pyridinyl]carbonyl]amino]-butanoic acid, ethyl ester

A solution of 450 mg (1.72 mmol) of Part E acid in 7 ml THF was cooled to 0° C. To this was added 161 μl (1.72 mmol, 1 eq.) of diethyl chlorophosphate, followed by 240 μl (1.72 mmol, 1 eq.) of triethylamine. The reaction was warmed to room temperature and stirred for 1 hour. Then ethyl-4-aminobutyrate hydrochloride, 317 mg (1.9 mmol, 1.1 eq.) was added, followed by 265 μl (1.9 mmol, 1.1 eq.) of triethylamine. The reaction was stirred an additional 2 hours at room temperature and then 5% $KHSO_4$ was added. The solution was extracted with EtOAc and the organic layers were washed with saturated NaCl. The organic layers were combined, dried ($Na_2SO_4$), filtered and concentrated in vacuo. The resulting residue was passed through a column of alumina (20×amount of combined starting materials, activity=1, 1:4 EtOAc/hexanes). The eluant was concentrated in vacuo and the crude material was purified by flash chromatography (9×3 cm, silia gel, 1:5 EtOAc/hexanes) to yield 412 mg (62%) of title product as a yellow oil.

IR (0.2 mm cells, $CCl_4$) 3403, 2957, 2929, 2856, 1736, 1680, 1520, 1253, 1178, 800 $cm^{-1}$.

270 MHz $^1$H NMR ($CDCl_3$) δ 0.80–1.6 (m, 18H); 2.00 (m, 2H); 2.30 (q, J=8, 2H); 2.43 (t, J=8, 2H); 3.52 (dt, J=7,7, 2H); 4.13 (q, J=7, 2H); 5.89 (dt, J=12,7, 1H); 6.40 (d, J=12, 1H); 7.70 (dd, J=8,2, 1H); 8.08 (br s, 1H); 8.13 (d, J=8, 1H); 8.43 (br s, $W_{\frac{1}{2}}$=5, 1H);

TLC (1:2 EtOAc/hexanes) $R_f$=0.31.

Microanalysis Calcd for $C_{22}H_{34}N_2O_3$: C, 70.58; H, 9.09; N, 7.48. Found: C, 70.69; H, 9.04; N, 7.15.

EXAMPLE 18

(Z)-4-[[[5-(1-Decenyl)-2-pyridinyl]carbonyl]amino]-butanoic acid

To a solution of 300 mg (0.80 mmol) of 4-[[[5-(1-decenyl)-2-pyridinyl]carbonyl]amino]butanoic acid, ethyl ester prepared as described in Example 17 in 24 ml of MeOH and 6 ml of THF, was added 664 mg of $K_2CO_3$ in 6 ml of $H_2O$. The reaction was stirred at room temperature overnight and 5% $KHSO_4$ was added. The solution was extracted with EtOAc. The organic extract was washed with saturated NaCl, dried ($Na_2SO_4$), filtered and concentrated in vacuo. A clear oil was obtained which solidified upon addition of hexanes and cooling to yield 270 mg (97%) of title acid as a white solid: m.p. 26°–28° C.

IR (0.2 mm $CCl_4$) 3399, 3017, 2929, 2856, 1711, 1680, 1521, 1252 $cm^{-1}$.

270 MHz $^1$H NMR ($CDCl_3$) δ 0.89 (t, 3H); 1.28 (m, 13H); 2.00 (m, 2H); 2.30 (q, J=7, 2H); 2.49 (t, J=7, 2H); 3.59 (dt, J=7, 7, 2H); 5.90 (dt, J=12, 7, 1H); 6.40 (d, J=12, 1H); 7.73 (dd, J=8, 2, 1H); 8.15 (br, 1H with d at 8.10, J=8, 1H); 8.43 (d, J=2, 1H).

EXAMPLE 19

4-[[[3-(1-Decenyl)-2-pyridinyl]carbonyl]amino]-butanoic acid, ethyl ester

A. 3-(1-Decenyl)-2-pyridinecarboxylic acid

To a solution containing 198 mg (0.82 mmol) of 2-cyano-5-decenylpyridine (prepared in Example 17 Parts A to C) in 4 ml EtOH, was added an equal volume of 10N NaOH. The reaction was refluxed for 2.5 hours, then cooled to room temperature and acidified with concentrated HCl to pH 1. The resulting slurry was filtered and the filtrate was concentrated in vacuo. To the resulting yellow solid was added $CHCl_3$ and the solution was filtered. The filtrate was concentrated in vacuo to yield 200 mg (93%) of title acid as a yellow viscous oil.

IR (KBr) 3276, 2928, 2856, 1769, 1553, 1458, 1431 $cm^{-1}$.

$^1$H NMR ($CDCl_3$) δ 0.45–2.78 (br m, 17H); 5.83 (m, 1H); 6.62–8.12 (br m, 4H); 11.8 (br s, 1H).

TLC (1:2 EtOAc/hexanes) $R_f$=0.58, UV.

B.
4-[[[3-(1-Decenyl)-2-pyridinyl]carbonyl]amino]-butanoic acid, ethyl ester

A solution of 200 mg (0.76 mmol) of Part A acid and 3 ml of THF was cooled to 0° C. and 71 μl (0.76 mmol, 1 eq.) of diethyl chlorophosphate was added, followed by 107 μl (0.76 mmol, 1 eq.) of triethylamine. The reaction was warmed to room temperature and stirred for 1 hour. To this solution was added 141 mg (0.84 mmol, 1.1 eq.) of ethyl-4-aminobutyrate hydrochloride, followed by 117 μl (0.84 mmol, 1.1 eq.) of triethylamine. The reaction was stirred for 2 hours at room temperature and EtOAc was added. This solution was washed with 5% KHSO$_4$, saturated NaCl and dried (Na$_2$SO$_4$). After filtration, the filtrate was concentrated in vacuo and the residue was passed through a column of alumina (20×amount of combined starting materials, activity=2, 1:4 EtOAc/hexanes). The eluant was concentrated and the crude material was purified by flash chromatography (9×3 cm, silica gel, 1:5 EtOAc/hexanes) to yield 142 mg (50%) of title ester as a colorless oil.

IR (film) 3410, 2930, 2850, 1750, 1680, 1520, 1170, 810 cm$^{-1}$.

$^1$H NMR (CDCl$_3$) δ 0.53–2.66 (br m, 25H) 3.46 (dd, J=7, 7, 2H); 4.20 (q, J=7, 2H); 5.72 (dt, J=11, 7, 1H); 7.07 (d, J=11, 1H); 7.25 (m, 1H); 8.10 (br s, 1H); 8.36 (dd, J=2, 4 Hz, 1H).

TLC (1:2 EtOAc/hexanes) R$_f$=0.29, PMA, UV.

Microanalysis Calcd for C$_{22}$H$_{34}$N$_2$O$_3$: C, 70.58; H, 9.09; N, 7.48. Found: C, 69.95; H, 8.98; N, 7.30.

EXAMPLE 20

(E)-4-[[[5-(1-Decenyl)-2-pyridinyl]carbonyl]amino]-butanoic acid, ethyl ester

A. 3-(1E-Decenyl)pyridine

To a solution of 22 g (47 mmol) of 1-triphenylphosphononyl bromide in 250 ml of dry THF at −78° was added dropwise 22 ml of (2.1M in hexane, 46 mmol) of n-butyllithium solution over 10 minutes. The reaction mixture was stirred at −78° for 1 hour then 50 ml (290 mmol) of dry HMPA was added followed by the addition of 4.3 g (40 mmol, Aldrich) of 3-pyridinecarboxaldehyde. The resulting dark solution was warmed to room temperature over 3 hours, stirred overnight then quenched with 5 ml of H$_2$O and concentrated in vacuo. The resulting dark residue was added to 200 ml of H$_2$O and extracted with two 100 ml portions of petroleum ether. The combined organic extracts were filtered, washed with three 150 ml portions of H$_2$O, dried (MgSO$_4$) and concentrated in vacuo. Flash chromatography (silica gel, 22×10 cm, 1:9 EtOAc/petroleum ether) afforded 4.36 g (50%) of title pyridine as a pale yellow liquid.

60 MHz $^1$H NMR (CDCl$_3$) δ 0.60–1.80 (m, 15H, —(CH$_2$)$_6$—CH$_3$); δ 1.85–2.45 (m, 2H, allylic —CH$_2$—); 6.32 (m, 2H, vinyl protons); 7.17 (dd, J=5,8, 1H, ring H$_5$); 7.65 (ddd, J=8,2,2,1H, ring H$_4$); 8.37 (dd, J=5,2,1H, ring H$_6$); 8.50 (d, J=2, 1H, ring H$_2$).

TLC: R$_f$ (silica gel, 1:5 EtOAc/petroleum ether)=0.32, UV and PMA. The cis isomer visualized as a minor product with an R$_f$ of 0.36.

B. 3-(1E-Decenyl)pyridine-N-oxide

To a solution of 4.30 g (19.8 mmol) of Part A pyridine in 40 ml of CH$_2$Cl$_2$ at −20° was added in 2 portions a total of 4.00 (85%, 20 mmol) of meta-chloroperoxybenzoic acid. The reaction mixture was stirred at −20° for 15 minutes then at 0° for 18 hours. The resulting solution was filtered through a column of 100 g of basic alumina (act I, 1:9 MeOH/CH$_2$Cl$_2$). The filtrate was concentrated in vacuo to afford crude N-oxide as an oil. Flash chromatography (silica gel, 16×5.0 cm, 1:19 MeOH/CH$_2$Cl$_2$) afforded 3.90 g (85%) of N-oxide as a pale yellow low melting solid.

270 MHz $^1$H NMR (CDCl$_3$) δ 0.88 (t, J=7, 3H, —CH$_3$) δ 1.15–1.58 (m, 12H, —CH$_2$(CH$_2$)$_6$CH$_3$); 2.23 (dt, J=7,7,2H, allylic —CH$_2$—); 6.21 (d, J=16, 1H, vinyl); 6.34 (dt, J=6,16,1H, vinyl); 7.21 (m, 2H, ring H$_4$ and H$_5$); 8.04 (d, J=6, 1H, ring H$_6$); 8.19 (s, 1H, ring H$_2$).

MS (CI): 234 (M+H)$^+$, 218 (M+H−O)$^+$.

C. (E)-2-Cyano-5-decenylpyridine and

D. (E)-2-Cyano-3-decenylpyridine

A solution of 3.35 g (14.4 mmol) of Part B N-oxide, 6.0 ml (45 mmol) of trimethylsilylcyanide, and 7.0 ml (50 mmol) of sieve-dried triethylamine in 15 ml of sieve-dried acetonitrile was heated at 100° (bath temperature) for 24 hours. The reaction mixture was cooled, quenched with 2 ml of H$_2$O, poured into 75 ml of H$_2$O and extracted with two 50 ml portions of petroleum ether. The combined organic extracts were dried (MgSO$_4$) and concentrated to give a dark oil. TLC analysis (1:9 EtOAc/petroleum ether) showed two major mobile spots. Purification by flash chromatography (silica gel, 20×5.0 cm, 1:14 EtOAc/petroleum ether) isolating the spot with higher R$_f$ afforded 1.02 g (29%) of title C nitrile as a yellow oil and the lower R$_f$ spot as 2.07 g (59%) of title D nitrile as a pale yellow solid.

Title C nitrile, 60 MHz $^1$H NMR (CDCl$_3$); δ 0.60–2.00 (m, 15H, —(CH$_2$)$_6$—CH$_3$); 2.05–2.65 (m, 2H, allylic —CH$_2$—); 6.50 (m, 2H, vinyl); 7.70 (M, 2H, ring H$_3$ and H$_4$); 8.72 (br s, 1H, ring H$_6$).

D. (E)-5-(1-Decenyl)-2-pyridinecarboxylic acid

A solution of 804 mg (3.32 mmol) of Part C nitrile in 4.0 ml of 10N aqueous NaOH and 4.0 ml of ethanol was refluxed for 2.5 hours. The reaction mixture was cooled, 3.5 ml (61 mmol) of glacial acetic acid was added followed by 10 ml of 50% aqueous ethanol. The resulting slurry was heated until homogeneous then allowed to cool slowly. The solid which formed was collected on a Buchner funnel, washed with 50% aqueous ethanol and vacuum-dried to afford 860 mg (100%) of title acid as a flaky, white solid.

TLC: R$_f$ (silica gel, 1:1:8 HOAc/MeOH/CH$_2$Cl$_2$)=0.46 (tails), UV.

E.

(E)-4-[[[5-(1-Decenyl)-2-pyridinyl]carbonyl]amino]-butanoic acid, ethyl ester

To a solution of 400 mg (1.53 mmol) of Part D ester in 10 ml of dry CH$_2$Cl$_2$ at 0° was added 0.25 ml (1.7 mmol) of diethyl chlorophosphate then 0.24 ml (1.7 mmol) of sieve-dried triethylamine. The reaction mixture was warmed to room temperature, stirred for 1.5 hours then an additional 0.24 ml (1.7 mmol) of triethylamine was added followed by 290 mg (1.74 mmol) of ethyl-4-aminobutyrate. After 2 hours, the reaction mixture was filtered through a small column of basic alumina (6.0×3.0 cm, 25 g, activity I) eluting with several column volumes of ethyl acetate. The eluant was concentrated in vacuo to afford 425 mg (74%) of crude title ethyl ester as a yellow ester.

60 MHz $^1$H NMR (CDCl$_3$) δ 0.60–2.70 (m, 24H, —nC$_8$H$_{17}$, —CH$_2$CH$_2$CO$_2$CH$_2$CH$_3$); δ 3.52 (dt, J=6,6,2H, —NH—CH$_2$—); 4.15 (q, J=7, 2H, —CO$_2$CH$_2$CH$_3$); 6.42 (m, 2H, vinyl); 7.75 (dd, J=2,8,1H, ring H$_4$); 8.12 (d with broad —NH— underneath, J for d=8, 2H, —NH—, ring H$_3$); 8.47 (d, J=2,1H, ring H$_6$).

TLC: R$_f$ (silica gel, 1:1 EtOAc/petroleum ether)=0.58, UV.

EXAMPLE 21

(E)-4-[[[5-(1-Decenyl)-2-pyridinyl]carbonyl]amino]-butanoic acid

A solution of 415 mg (1.10 mmol) of crude Example 20 ethyl ester and 80 mg (1.9 mmol) of lithium hydroxide monohydrate in 5 ml of 1:4 H$_2$O/THF was stirred at room temperature for 16 hours then 0.15 ml (2.6 mmol) of glacial HOAc was added to the reaction mixture. The resulting solution was added to 15 ml of H$_2$O and extracted with 15 ml of ethyl acetate. The organic layer was separated, washed with an additional 15 ml of H$_2$O, dried (MgSO$_4$) and concentrated in vacuo to give an oil. Flash chromatography (silica gel, 12×3.0 cm, 1:9 MeOH/CH$_2$Cl$_2$) yielded 248 mg (68%) of product. Recrystallization (ether/petroleum ether) of a portion afforded title acid as a microcrystalline white powder, m.p. 35°–37°.

IR: 3309, 2925, 1703, 1649, 1529, 1206 cm$^{-1}$.

270 MHz $^1$H NMR (CDCl$_3$) δ 0.88 (t,J=7,3H, —CH$_3$); δ 1.10–1.60 (m, 10H, —(CH$_2$)$_5$—CH$_3$); 1.99 (tt, J=7,7,2H, —NH—CH$_2$—CH$_2$—CH$_2$—); 2.26 (m, 2H, allylic —CH$_2$—); 2.47 (t, J=7,2H, —CH$_2$CO$_2$H); 3.56 (dt, J=7,7,2H, —NH—CH$_2$—); 6.40 (m, 2H, vinyl); 7.78 (dd, J=2,8,1H, ring H$_4$); 8.17 (m, 1H, —NH—); 8.45 (d, J=2, 1H, ring H$_6$);

Partial 67.5 MHz $^{13}$C NMR (CDCl$_3$) δ 122.28, 125.57, 133.52, 135.95, 136.17, 146.11, 147.64, 164.83, 177.47.

MS (CI): 347 (M+H)$^+$.

TLC: R$_f$ (silica gel, 1:9 MeOH/CH$_2$Cl$_2$)=0.45, UV and PMA.

Analysis Calculated for C$_{20}$H$_{30}$N$_2$O$_3$: C, 69.33; H, 8.73; N, 8.09. Found: C, 68.63; H, 8.65; N, 7.77.

EXAMPLE 22

4-[[[4-(Nonyloxy)-2-pyridinyl]carbonyl]amino]butanoic acid, ethyl ester

A. 4-Nonyloxypyridine-N-oxide

An oil dispersion of 215 mg (50%, 4.5 mmol) of sodium hydride was washed several times with petroleum ether to remove the oil, then 5 ml of sieve-dried DMF was added followed by 650 mg (4.51 mmol, Aldrich) of 1-nonanol. The reaction mixture was warmed gently until H$_2$ evolution ceased (~½ hour), then 500 mg (3.86 mmol, Aldrich) of 4-chloropyridine-N-oxide was added in 1 portion. The reaction mixture was heated to 60° for 1 hour, then added to 20 ml of saturated aqueous NaCl solution and extracted with two-20 ml portions of ethyl acetate. The organic extracts were combined, dried (MgSO$_4$) and concentrated in vacuo to afford a dark oil. Flash chromatography (silica gel, 15×5.0 cm, 1:19 MeOH/CH$_2$Cl$_2$) of the crude material gave 600 mg (66%) of title N-oxide as a white solid, m.p. 75°–77°.

IR(KBr) 2920, 1619, 1488, 1467, 1292, 1282, 1219, 1006, 787 cm$^{-1}$.

60 MHz $^1$H NMR (CDCl$_3$) δ 0.60–2.25 (m, 17H); δ 3.98 (t, J=6, 2H, —O—CH$_2$—(CH$_2$)$_7$—CH$_3$); 6.75 (d, J=8, 2H, ring H$_3$ and H$_4$); 8.08 (d, J=8, 2H, ring H$_2$ and H$_6$).

MS(CI): 238 (M+H)$^+$, 222 (loss of 0).

TLC: R$_f$ (silica gel, 1:9 MeOH/CH$_2$Cl$_2$)=0.34, UV and PMA. The R$_f$ of title A N-oxide under identical conditions was 0.43.

B. 2-Cyano-4-nonyloxypyridine

A solution of 480 mg (2.03 mmol) of Part A N-oxide, 2.4 ml (18 mmol) of trimethylsilylcyanide, 2.5 ml (18 mmol) of sieve-dried triethylamine and 7 ml of sieve-dried acetonitrile was heated to reflux for 48 hours. The dark reaction mixture was cooled, added to 25 ml of H$_2$O and extracted with 25 ml of ethyl acetate. The organic extract was dried (MgSO$_4$), concentrated in vacuo and purified by flash chromatography (silica gel, 12×3.0 cm, 1:6 EtOAc/petroleum ether) to afford 370 mg (74%) of title nitrile as a low melting solid, m.p. 35°–37°.

IR(melt) 2865, 2242, 1597, 1460, 1309, 1276, 1157, 1111, 1010 cm$^{-1}$.

60 MHz $^1$H NMR (CDCl$_3$) δ 0.70–2.25 (m, 17H); δ 4.03 (t, J=6, 2H, —OCH$_2$—(CH$_2$)$_7$CH$_3$); 6.97 (dd, J=2, 6 1H, ring H$_5$); 7.20 (d, J=2, 1H, ring H$_3$); 8.50 (d, J=6, 1H, ring H$_6$).

MS(CI): 247 (M+H)$^+$.

TLC: R$_f$ (silica gel, 1:4 EtOAc/petroleum ether)=0.57, UV.

C. 4-Nonyloxy-2-pyridinecarboxylic acid

A solution of 340 mg (1.38 mmol) of Part B nitrile in 3 ml of 10M aqueous NaOH solution and 7 ml of ethanol was refluxed for 30 minutes. The reaction mixture was cooled, and concentrated HCl (~2.5 ml) was added until pH=1. The resulting slurry was added to 15 ml of H$_2$O and extracted with two-15 ml portions of hot ethyl acetate. The organic extracts were combined and cooled at 0°. The crystals which formed were collected by filtration, washed with cold ethyl acetate and dried under vacuum to afford 281 mg (77%) of title acid as white crystals, m.p. 89°–92°.

IR(KBr) 3370 (broad), 2915, 1624, 1598, 1478, 1384, 1337, 1337 cm$^{-1}$.

60 MHz $^1$H NMR (CDCl$_3$,d$_6$DMSO) δ 0.65–2.25 (m, 17H); δ 4.15 (t, J=6, 2H, —O—CH$_2$—(CH$_2$)$_7$—CH$_3$); 7.05 (dd, J=2, 6, 1H, ring H$_5$); 7.75 (d, J=2, 1H, ring H$_3$); 8.67 (d, J=6, 1H, ring H$_6$);

MS(CI): 266 (M+H)$^+$.

D. 4-[[[4-(Nonyloxy)-2-pyridinyl]carbonyl]amino]butanoic acid, ethyl ester

To a solution of 250 mg (0.94 mmol) of Part C acid in 10 ml of dry CH$_2$Cl$_2$ cooled to 0° was added 0.20 ml (1.4 mmol) of diethyl chlorophosphate, then 0.20 ml (1.4 mmol) of sieve-dried triethylamine. The reaction mixture was warmed to room temperature and after 1 hour, an additional 0.20 ml (1.4 mmol) of triethylamine was added, followed by 250 mg (1.49 mmol) of ethyl-4-aminobutyrate hydrochloride. The resulting solution was stirred for 2.5 hours, then filtered through a small column (10×2 cm) of basic alumina (act I) eluting with ethyl acetate. The eluant was concentrated in vacuo to afford 300 mg (84%) of crude title ester as a pale yellow oil.

IR (film) 3289, 2865, 1736, 1675, 1603, 1520, 1460, 1300, 1027 cm$^{-1}$.

60 MHz $^1$H NMR (CDCl$_3$)δ 0.60–2.70 (m, 24H); δ 3.52 (dt, J=6, 6, 2H, —NH—CH$_2$); 4.07 (t, J=6, 2H, —O—CH$_2$—(CH$_2$)$_7$—CH$_3$); 4.18 (t, J=6, 2H, —CH$_2$—CO$_2$CH$_2$—CH$_3$); 6.87 (dd, J=2, 6, 1H, ring H$_5$); 7.73 (d, J=2, 1H, ring H$_3$); 8.16 (br s, 1H, —NH—); 8.33 (d, J=6, 1H, ring H$_6$).

TLC: $R_f$ (silica gel, 1:1 EtOAc/petroleum ether)=0.50, UV.

EXAMPLE 23

4-[[[4-(Nonyloxy)-2-pyridinyl]carbonyl]amino]butanoic acid

A solution of 300 mg (0.79 mmol) of Example 22 ester and 70 mg (1.7 mmol) of LiOH·H$_2$O in 3 ml of THF and 1 ml of H$_2$O was stirred rapidly for 16 hours. The reaction mixture was acidified with 1M HCl to pH=2, added to 15 ml of H$_2$O and extracted with two 15 ml portions of ether. The organic extracts were combined, dried (MgSO$_4$) and concentrated in vacuo to give a solid. Recrystallization (ether/petroleum ether) afforded 220 mg (80%) of title acid as fluffy white needles, m.p. 66°–68°.

IR(KBr) 3337 (broad), 2920, 1696, 1653, 1606, 1533, 1310 cm$^{-1}$.

270 MHz $^1$H NMR (CDCl$_3$) δ 0.88 (t, J=7, 3H, —CH$_3$); δ 1.10–1.55 (m, 12H); 1.80 (tt, J=7, 7, 2H, —OCH$_2$—CH$_2$CH$_2$—); 1.99 (tt, J=7, 7, 2H, —NH—CH$_2$13 CH$_2$—CH$_2$—); 2.47 (t, J=7, 2H, —CH$_2$COOH); 3.54 (dt,J=7, 7, 2H, —NH—CH$_2$—CH$_2$—); 4.07 (t, J=7, 2H, —OCH$_2$—CH$_2$—); 6.90 (dd, J=2, 6, 1H, ring H$_5$); 7.71 (d, J=2, 1H, ring H$_3$); 8.30 (d with broad s underneath, J=6, 2H, ring H$_6$ and —NH—); 9.80 (br s, 1H, —COOH).

67.5 MHz $^{13}$C NMR (CDCl$_3$)δ 14.03, 22.62, 24.80, 25.83, 28.79, 29.18, 29.23, 29.43, 31.38, 31.80, 38.75, 68.52, 108.27, 113.38, 148.98, 151.63, 164.72 166.64, 177.41.

MS(CI): 351 (M+H)$^+$.

TLC: $R_f$(silica gel, 1:9 MeOH/CH$_2$Cl$_2$)=0.64, UV.

Analysis Calcd for C$_{19}$H$_{30}$N$_2$O$_4$: C, 65.12; H, 8.63; N, 7.99. Found: C, 64.97; H, 8.61; N, 7.93.

EXAMPLE 24

4-[[(4-Phenyl-2-pyridinyl)carbonyl]amino]butanoic acid, ethyl ester

A. 4-Phenyl-2-pyridinecarboxylic acid (1) 2-Cyano-4-phenylpyridine

A solution of 1.90 g (11.1 mmol) of 4-phenylpyridine-N-oxide (available from Aldrich Chemical Co.), 4.8 ml (35 mmol) of sieve-dried triethylamine and 4.7 ml (35 mmol) trimethylsilylcyanide in 10 ml of sieve-dried acetonitrile was heated to 100° for 24 hours. The reaction mixture was cooled, quenched with 1 ml of H$_2$O then added to 50 ml of H$_2$O and extracted with three-25 ml portions of ethyl acetate. The organic extracts were combined, dried (MgSO$_4$), concentrated in vacuo and purified by flash chromatography (silica gel, 1:4 EtOAc/petroleum ether) to give 2-cyano-4-phenylpyridine as a white solid. Recrystallization (EtOAc/petroleum ether) of the solid afforded 1.65 g (83%) of title nitrile as white crystals, m.p. 97°–98°.

IR(KBr) 3053, 2234, 1590, 1541, 1498, 1461, 1389, 1284, 848, 761, 694 cm$^{-1}$.

60 MHz $^1$H NMR (CDCl$_3$)δ 7.23–7.85 (m, 6H, phenyl and pyridine ring H$_5$); δ 7.93 (crude d, J=2, 1H, pyridine ring H$_3$); 8.77 (d, J=5, 1H, pyridine ring H$_6$).

TLC: $R_f$ (silica gel, 1:2 EtOAc/petroleum ether)=0.59, UV.

(2) 4-Phenyl-2-pyridinecarboxylic acid

A solution of 1.00 g (5.55 mmol) of Part A (1) nitrile in 10 ml of ethanol and 5.0 ml of 10M aqueous NaOH was heated to 80°–85° for 2 hours. The reaction mixture was cooled, acidified to pH=2 with concentrated HCl and the resulting slurry added to 50 ml of H$_2$O, then extracted with three 25 ml portions of hot ethyl acetate. The combined organic extracts were dried (MgSO$_4$) and concentrated in vacuo to give a white solid. Recrystallization (EtOAc/petroleum ether) of the crude material afforded 899 mg (81%) of title acid as white crystals, m.p. 155°–157°.

IR(KBr) 3433, 3100, 2400 (broad), 1728, 1619, 1603, 1312, 1227, 766 cm$^{-1}$.

270 MHz $^1$H NMR (d$_6$-DMSO)δ 7.54 (m, 3H, phenyl meta and para); δ 7.86 (dd, J=2, 8, 2H, phenyl ortho); 7.96 (dd, J=1, 5, 1H, pyridine ring H$_5$); 8.30 (d, J=1, 1H, pyridine ring H$_3$); 8.77 (d, J=5, 1H, pyridine ring H$_6$).

MS(CI): 200 (M+H)$^+$.

TLC: $R_f$ (silica gel, 1:1:8 HOAc/MeOH/CH$_2$Cl$_2$)=0.57 (tails), UV.

Microanalysis Calcd for C$_{12}$H$_9$NO$_2$: C, 72.35; H, 4.55; N, 7.03. Found: C, 72.02; H, 4.58; N, 7.10.

B. 4-[[(4-Phenyl-2-pyridinyl)carbonyl]amino]butanoic acid, ethyl ester

To a solution of 199 mg (1.00 mmol) of Part A acid in 10 ml of dry CH$_2$Cl$_2$ cooled to 0° was added 200 μl (1.38 mmol) of diethyl chlorophosphate and then 200 μl (1.4 mmol) of sieve-dried triethylamine. The reaction mixture was warmed to room temperature, stirred for 1 hour, then an additional 200 μl (1.4 mmol) of triethylamine was added followed by 235 mg (1.40 mmol) of ethyl-4-aminobutyrate hydrochloride. The resulting solution was stirred for 2 hours, then concentrated in vacuo to ½ volume and diluted with 10 ml of ethyl acetate to precipitate triethylamine hydrochloride. The resulting slurry was filtered through a column of basic alumina (12 g, activity I) eluting with several column volumes of ethyl acetate. The filtrate was concentrated in vacuo to afford 250 mg (80%) of crude title ester as a yellow oil.

IR (neat) 3300, 2915, 1730, 1672, 1524, 1245, 1176, 1025, 761 cm$^{-1}$.

60 MHz $^1$H NMR (CDCl$_3$)δ 1.23 (t, J=7, 3H, —CO$_2$CH$_2$CH$_3$); δ 1.60–2.75 (m, 4H, —(CH$_2$)$_2$CO$_2$Et); 3.57 (dt, J=7,7 2H, —NH—CH$_2$—); 4.12 (q, J=7, 2H, —CO$_2$CH$_2$CH$_3$); 7.30–7.90 (m, 6H, phenyl and pyridine ring H$_5$); 8.20 (br s, 1H, —NH—); 8.45 (d, J=2, 1H, pyridine ring H$_3$); 8.58 (d, J=5, 1H, pyridine ring H$_6$).

TLC: $R_f$(silica gel, 1:9 MeOH/CH$_2$Cl$_2$)=0.19, UV.

EXAMPLE 25

4-[[(4-Phenyl-2-pyridinyl)carbonyl]amino]butanoic acid

A solution of 210 mg (0.67 mmol) of Example 24 ester and 56 mg (1.3 mmol) of lithium hydroxide monohydrate in 3 ml of 2:1 THF/H$_2$O was stirred rapidly at room temperature for 16 hours. The resulting solution was acidified with 1M aqueous HCl to pH=2, added to 15 ml of H$_2$O and extracted with 15 ml of ethyl acetate. The organic layer was dried (MgSO$_4$) and concentrated in vacuo to give an oil. The crude oil was crystallized (EtOAc/petroleum ether) to afford 170 mg (89%) of title acid as small white crystals, m.p. 123°–124°.

IR (KBr) 3342, 3031, 1724, 1642, 1598, 1534, 1187, 760 cm$^{-1}$.

270 MHz $^1$H NMR (CDCl$_3$)δ 2.01 (tt, J=7,7, 2H, —NHCH$_2$—CH$_2$—); δ 2.50 (t, J=7, 2H, —CH$_2$COOH); 3.59 (dt, J=7,7, 2H, —NH—CH$_2$—);

7.35–7.56 (m, 3H, phenyl); 7.63 (dd, J=1,5, 1H, pyridine ring H₅); 7.70 (dd, J=2,8,2H phenyl 2,2′); 8.32 (crude t, 1H, —NH—); 8.45 (d, J=1, 1H, pyridine ring H₃); 8.55 (d, J=5, 1H, pyridine ring H₆).

67.5 MHz $^{13}$C NMR (CDCl$_3$)δ 24.85, 31.47, 38.78, 120.30, 123.84, 127.05 (strong), 129.17 (strong), 129.48, 137.26, 148.48, 150.01, 150.24, 164.80, 177.63.

MS(CI): 285 (M+H)⁺.

TLC: R$_f$(silica gel, 1:9 MeOH/CH$_2$Cl$_2$)=0.31, UV.

Microanalysis Calcd for C$_{26}$H$_{16}$N$_2$O$_3$: C, 67.59; H, 5.67; N, 9.85. Found: C, 67.34; H, 5.62; N, 9.67.

EXAMPLE 26

[[(5-Heptyl-2-pyridinyl)carbonyl]amino]hexanoic acid

Following the procedure of Examples 9 and 10 except substituting 1-triphenylphosphohexyl bromide for 1-triphenylphosphononyl bromide, and substituting ethyl 6-amino hexanoate bromide for β-alanine ethyl ester hydrochloride, the title compound is obtained.

EXAMPLE 27

[[(3-Undecyl-2-pyridinyl)carbonyl]amino]acetic acid

Following the procedure of Examples 1 and 2 except substituting 3-pyridine carboxaldehyde for 4-pyridine carboxaldehyde and 1-triphenylphosphodecyl bromide for 1-triphenylphosphononyl bromide, the title compound is obtained.

EXAMPLE 28

[[(6-Nonyl-2-pyridinyl)carbonyl]amino]nonanoic acid

Following the procedure of Examples 1 and 2 except substituting 6-pyridinecarboxaldehyde for 4-pyridine carboxaldehyde, 1-triphenylphosphooctyl bromide for 1-triphenylphosphononyl bromide, and substituting ethyl-9-amino nonanoate bromide for glycine ethyl ester hydrochloride, the title compound is obtained.

EXAMPLE 29

8-[[[5-(1-Dodecenyl)-2-pyridinyl]carbonyl]amino]octanoic acid

Following the procedure of Examples 17 and 18 except substituting 1-triphenylphosphoundecyl bromide for 1-triphenylphosphononyl bromide, and ethyl 8-aminooctanoate bromide for ethyl 4-aminobutyrate hydrochloride, the title compound is obtained.

EXAMPLE 30

[[[(4-(1-Octenyl)-2-pyridinyl]carbonyl]amino]acetic acid

Following the procedure of Examples 17 and 18 except substituting 4-pyridinecarboxaldehyde for 5-pyridinecarboxaldehyde, and 1-triphenylphosphoheptyl bromide for 1-triphenylphosphononyl bromide, the title compound is obtained.

EXAMPLE 31

[[(4-Tridecyloxy-2-pyridinyl)carbonyl]amino]acetic acid

Following the procedure of Examples 22 and 23 except substituting tridecyl alcohol for nonyl alcohol, and substituting glycine ethyl ester hydrochloride for ethyl 4-aminobutyrate hydrochloride, the title compound is obtained.

EXAMPLE 32

5-[[[5-(Decyloxy)-2-pyridinyl]carbonyl]amino]pentanoic acid

Following the procedure of Examples 22 and 23 except substituting 5-chloropyridine N-oxide for 4-chloropyridine N-oxide, decyl alcohol for nonyl alcohol, and substituting ethyl 5-aminovalerate hydrochloride for ethyl 4-aminobutyrate hydrochloride, the title compound is obtained.

EXAMPLE 33

[[(4-Phenyl-2-pyridinyl)carbonyl]amino]acetic acid

Following the procedure of Examples 24 and 25 except substituting glycine ethyl ester, hydrochloride for ethyl 4-aminobutyrate hydrochloride, the title compound is obtained.

EXAMPLE 34

[[(4-Pentadecyl-2-pyridinyl)carbonyl]amino]acetic acid

Following the procedure of Examples 1 and 2 except substituting 1-triphenylphosphotetradecyl bromide for 1-triphenylphosphononyl bromide, the title compound is obtained.

EXAMPLE 35

6-[[(5-Phenyl-2-pyridinyl)carbonyl]amino]hexanoic acid

Following the procedure of Examples 24 and 25 except substituting 5-pyridinecarboxaldehyde for 4-pyridinecarboxaldehyde, and substituting ethyl 6-aminohexanoate hydrochloride for ethyl 4-aminobutyrate hydrochloride, the title compound is obtained.

EXAMPLE 36

[[[(6-(1-Heptenyl)-2-pyridinyl]carbonyl]amino]acetic acid

Following the procedure of Examples 15 and 16 except substituting 6-pyridinecarboxaldehyde for 5-pyridinecarboxaldehyde, and substituting glycine ethyl ester hydrochloride for ethyl 4-aminobutyrate hydrochloride, the title compound is obtained.

EXAMPLE 37

9-[[(3-Phenyl-2-pyridinyl)carbonyl]amino]nonanoic acid

Following the procedure of Examples 24 and 25 except substituting 3-pyridinecarboxaldehyde for 4-pyridinecarboxaldehyde, and substituting ethyl 9-aminononanoate hydrochloride for ethyl 4-aminobutyrate hydrochloride, the title compound is obtained.

EXAMPLE 38

[[(6-Phenyl-2-pyridinyl)carbonyl]amino]decanoic acid

Following the procedure of Examples 24 and 25 except substituting 6-pyridinecarboxaldehyde for 4-pyridinecarboxaldehyde, and substituting ethyl 1-aminodecanoate hydrochloride for ethyl 4-aminobutyrate hydrochloride, the title compound is obtained.

EXAMPLE 39

[[(4-Nonadecyl-2-pyridinyl)carbonyl]amino]heptanoic acid

Following the procedure of Examples 1 and 2 except substituting 1-triphenylphosphooctadecyl bromide for 1-triphenylphosphononyl bromide, and substituting ethyl 7-amino-heptanoate bromide hydrochloride for glycine ethyl ester hydrochloride, the title compound is obtained.

EXAMPLE 40

[[(4-Octyl-2-pyridinyl)carbonyl]amino]decanoic acid

Following the procedure of Examples 1 and 2 except substituting 1-triphenylphosphoheptyl bromide for 1-triphenylphosphononyl bromide, and substituting ethyl 10-amino decanoate bromide for glycine ethyl ester hydrochloride, the title compound is obtained.

What is claimed is:

1. A compound having the structure

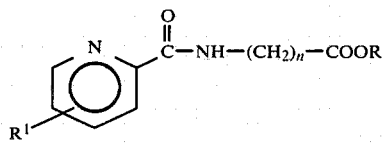

wherein n is 1 to 10,

R is hydrogen, lower alkyl, alkali metal or an amine salt; and $R^1$ is $C_6$–$C_{20}$ alkyl, $C_6$–$C_{20}$ alkenyl, $C_6$–$C_{20}$ alkoxy or phenyl, including pharmaceutically acceptable salts thereof.

2. The compound as defined in claim 1 wherein $R^1$ is in the 4- or 5-position on the pyridine ring.

3. The compound as defined in claim 1 wherein $R^1$ is $C_8$ to $C_{14}$ alkyl, $C_8$ to $C_{14}$ alkenyl, $C_8$ to $C_{14}$ alkoxy or phenyl.

4. The compound as defined in claim 1 wherein $R^1$ is n-decyl, n-tridecyl, 1-decenyl, phenyl or nonyloxy.

5. The compound as defined in claim 1 having the name [[4-decyl-2-pyridinyl)carbonyl]amino]acetic acid or its ethyl ester.

6. The compound as defined in claim 1 having the name 3-[[(4-decyl-2-pyridinyl)carbonyl]amino]propanoic acid or its ethyl ester.

7. The compound as defined in claim 1 having the name 4-[[(4-decyl-2-pyridinyl)carbonyl]amino]butanoic acid or its ethyl ester.

8. The compound as defined in claim 1 having the name 5-[[(4-decyl-2-pyridinyl)carbonyl]amino]pentanoic acid or its ethyl ester.

9. The compound as defined in claim 1 having the name 3-[[(5-decyl-2-pyridinyl)carbonyl]amino]propanoic acid or its ethyl ester.

10. The compound as defined in claim 1 having the name 4-[[(5-decyl-2-pyridinyl)carbonyl]amino]butanoic acid or its ethyl ester.

11. The compound as defined in claim 1 having the name 4-[[(5-decyl-2-pyridinyl)carbonyl]amino]pentanoic acid or its ethyl ester.

12. The compound as defined in claim 1 having the name 4-[[[5-(1-tridecenyl)-2-pyridinyl]carbonyl]amino]butanoic acid.

13. The compound as defined in claim 1 having the name 4-[[(5-tridecyl-2-pyridinyl)carbonyl]amino]butanoic acid.

14. The compound as defined in claim 1 having the name 4-[[[5-(1-decenyl)-2-pyridinyl]carbonyl]amino]butanoic acid or its ethyl ester.

15. The compound as defined in claim 1 having the name 4-[[(3-(1-decenyl)-2-pyridinyl]carbonyl]amino]butanoic acid or its ethyl ester.

16. The compound as defined in claim 1 having the name 4-[[[4-(nonyloxy)-2-pyridinyl]carbonyl]amino]butanoic acid or its ethyl ester.

17. The compound as defined in claim 1 having the name 4-[[(4-phenyl-2-pyridinyl)carbonyl]amino]butanoic acid or its ethyl ester.

18. A composition for inhibiting allergic conditions mediated by leukotrienes in a mammalian species, comprising an effective amount of a compound as defined in claim 1 or a pharmaceutically acceptable salt thereof, and a pharmaceutically acceptable carrier thereof.

19. A method of inhibiting arachidonic acid release, which comprises administering to the circulatory system of a mammalian host an effective amount of a compound as defined in claim 1 or a pharmaceutically acceptable salt thereof.

20. The method as defined in claim 19 wherein said compound is administered in an amount within the range of from about 1 to about 100 mg/kg.

21. A method for treating asthma mediated by leukotrienes in a mammalian species in need of such treatment, which comprises administering to a mammalian host an effective amount of a compound as defined in claim 1 or a pharmaceutically acceptable salt thereof.

* * * * *